(12) United States Patent
Fukusaki et al.

(10) Patent No.: US 8,921,654 B2
(45) Date of Patent: Dec. 30, 2014

(54) **GENE CLUSTER INVOLVED IN BIOSYNTHESIS OF ISOPENTENYL DIPHOSPHATE IN THE NON-MEVALONATE PATHWAY OF *HEVEA BRASILIENSIS***

(75) Inventors: Eiichiro Fukusaki, Osaka (JP); Tomoki Sando, Tokyo (JP); Norie Watanabe, Tokyo (JP); Akio Kobayashi, Osaka (JP); Teuku Tajuddin, Tangerang (ID)

(73) Assignee: Bridgestone Corporation, Tokyo (JP)

( * ) Notice: Subject to any disclaimer, the term of this patent is extended or adjusted under 35 U.S.C. 154(b) by 1155 days.

(21) Appl. No.: 12/874,996

(22) Filed: Sep. 2, 2010

(65) Prior Publication Data

US 2011/0083230 A1    Apr. 7, 2011

Related U.S. Application Data

(62) Division of application No. 11/522,391, filed on Sep. 18, 2006, now Pat. No. 7,803,985.

(30) Foreign Application Priority Data

Sep. 16, 2005  (JP) ................................ 2005-270066
Sep. 4, 2006   (JP) ................................ 2006-238822

(51) Int. Cl.
| | |
|---|---|
| *C12N 15/29* | (2006.01) |
| *C12N 15/52* | (2006.01) |
| *C12N 15/82* | (2006.01) |
| *A01H 5/00* | (2006.01) |
| *C12N 9/10* | (2006.01) |
| *C12N 9/12* | (2006.01) |
| *C12N 9/92* | (2006.01) |
| *C12N 9/02* | (2006.01) |

(52) U.S. Cl.
CPC ............ *C12N 9/1205* (2013.01); *C12N 9/1022* (2013.01); *C12N 9/1241* (2013.01); *C12N 9/92* (2013.01); *C12N 15/52* (2013.01); *C12N 9/0093* (2013.01); *C12N 15/8243* (2013.01); *C12N 9/1085* (2013.01)
USPC ......... 800/284; 800/298; 536/23.1; 536/23.2; 536/23.6; 435/183

(58) Field of Classification Search
None
See application file for complete search history.

(56) References Cited

FOREIGN PATENT DOCUMENTS

| | | |
|---|---|---|
| DE | 19752700 A | 6/1999 |
| DE | 19845231 A1 | 4/2000 |
| WO | 00/32792 A3 | 6/2000 |
| WO | 00/44912 A1 | 8/2000 |
| WO | 01/09341 A3 | 2/2001 |

OTHER PUBLICATIONS

Sando T, et al. Biosci. Biotechnol. Biochem. (2008); vol. 72, No. 11; pp. 2903-2917.*
Okada K. et al. Planta (2002) vol. 215, pp. 339-344.*
Japanese Office Action corresponding to JP Application No. 2006-238822, dated Jan. 24, 2012.
J-H Ko et al., Transcriptome analysis reveals novel features of the molecular events occurring in the laticifers of *Heavea brasiliensis* (para rubber tree), Plant Molecular Biology vol. 53, 2003, pp. 479-492 with Abstract.
NCBI Sequence Accession No: AY502939, May 1, 2007, Y Seetang-Nun, "Hevea brasiliensis putative 1-deoxy-D-xylulose 5-phosphate synthase", available at http://www.ncbi.nlm.noh.gov.
French Office Action for corresponding Application No. 0608144, issued Feb. 7, 2013.
Krushkal J et al: "Computational analysis of the evolution of the structure and function of 1-deoxy-D-xylulose-5-phosphate synthase, a key regulator of the mevalonate-independent pathway in plant" Gene 313 (2003) 127-138.
Bouvier F et al: "Biogenesis, molecular regulation and function of plant isoprenoids", Progress in Lipid Research 44 (2005) 357-429.

* cited by examiner

*Primary Examiner* — Russell Kallis
(74) *Attorney, Agent, or Firm* — Sughrue Mion, PLLC

(57) ABSTRACT

According to this invention, a gene cluster involved in the non-mevalonate pathway of *Hevea brasiliensis* was obtained and nucleotide sequences of these genes were determined. The gene cluster according to this invention involved in the IPP biosynthesis in the non-mevalonate pathway is involved in the biosynthesis of vitamin E and carotenoids. Therefore, the *Hevea brasiliensis* obtained by introducing the gene cluster of the present invention can be expected to produce high-quality rubber with improved permanence.

7 Claims, 4 Drawing Sheets

FIG. 2
1- deoxy-D-xylulose-5-phospho reductoisomerase
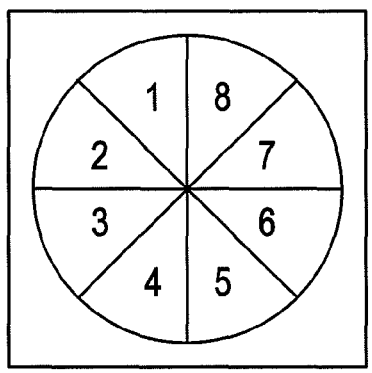
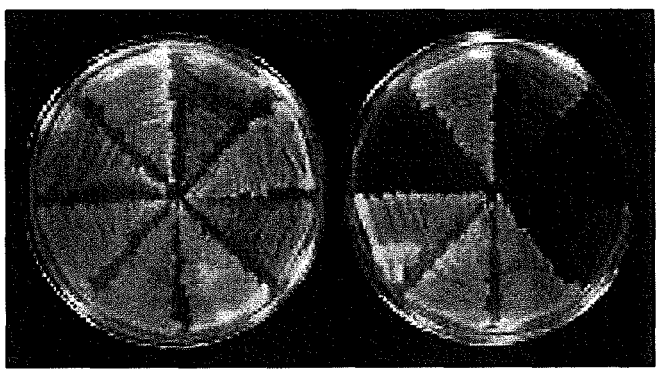
LB + ME　　　LB

FIG. 3
2-C-methyl-D-erythritol-4-phospho cytidyltransferase
LB + MVA    LB
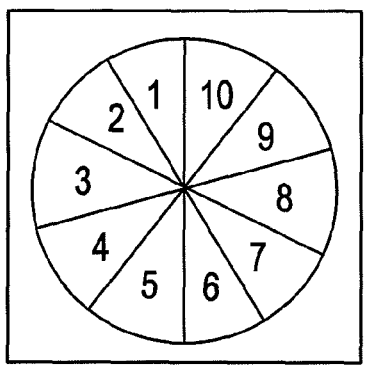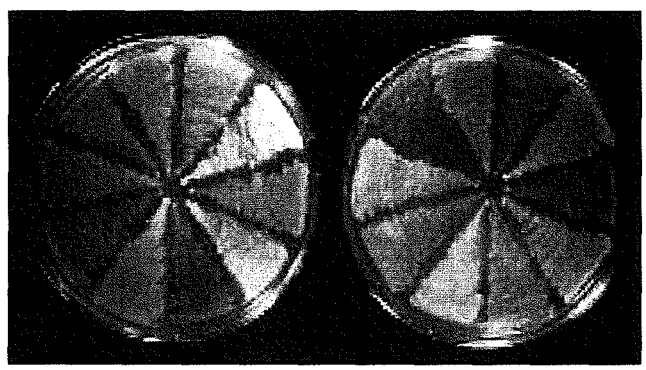

2-C-methyl-D-erythritol-2,4- cyclodiphospho synthase

SEQUENCE LISTING

```
<160> NUMBER OF SEQ ID NOS: 18

<210> SEQ ID NO 1
<211> LENGTH: 2591
<212> TYPE: DNA
<213> ORGANISM: Hevea brasiliensis
<220> FEATURE:
<221> NAME/KEY: MOD_RES
<222> LOCATION: (2481)
<223> OTHER INFORMATION: a, c, g, t, unknown or other

<400> SEQUENCE: 1
tgacttggtc ccgctcctaa aaccctctcg acatcttctt tgttggccac cacaagctga      60
ttttaatact gaatcacctc ctcaatagtg gtgcattcgg acccataatc acaatctcca     120
ttgtgttttt gtttctgggt tcttcttcct cttcttttta tctctattca caatttcgaa     180 ctgttttga actctttttg ttgcttgctt gcttctgttg gttctctatc tgtgatggct     240
ctctctgcgt gttcatttcc tgctcatgta gataaagcca caatctcaga tcttcaaaag     300
tacggttatg tcccttctcg ttccttatgg agaacagatc tgttggccca gtctcttggc     360
agactcaatc aggcaaagag caagaaaggg ccgggtggga tttgtgcatc actgtcagag     420
agaggagaat atcactctca gagaccacca accccctctct tggataccac aaactatcca     480
attcatatga aaaatctatc aatcaaggaa ctaaagcaac tagcagacga gctgcggtcc     540
gatgttattt tcaatgtttc tagaactggg ggtcacttag gatcaagcct tggtgttgtt     600
gagctcactg tggctcttca ctatgttttc agtgctcctc gagacaagat actgtgggat     660
gttggccatc agtcctaccc tcacaaaatc ctgactggga gaagagaaaa gatgtacaca     720
atcagacaga caaatggact ttctggtttc acgaagcgat cagagagtga atatgattgc     780
tttgggactg gtcatagctc taccactatt tctgcaggct tggggatggc agttgggaga     840
gatttaaaag gaaaaaagaa caacgtagtt gctgttatag gtgatggtgc catgacagca     900
ggacaagctt atgaagctat gaacaatgca gggtatcttg actctgatat gattgttatt     960
cttaatgaca caaacaagt ttctttaccg actgctactc ttgatggacc cataccacca    1020
gtgggagctt tgagcagtgc tcttagtagg ttgcaatcaa ataggcctct cagggaacta    1080
agagaggttg ctaagggtgt tacaaagcag attggtggac ccatgcatga atgggcagca    1140
aaggttgatg aatatgctcg tgggatgatc agtggttctg gatcaaccct ctttgaagag    1200
cttggattat attatattgg tcctgttgat ggccacaaca tagatgatct tatagctatt    1260
ctcaaagagg ttaagagtac taaaacaact ggtccagtct tgatacacgt tgtcactgag    1320
aaaggtcggg gatatccata tgctgagaaa gctgcagata agtaccacgg ggttaccaag    1380
tttgatcctg caactggaaa acaattcaag ggcagtgcta ttacacagtc ttacactaca    1440
```

```
tactttgcag aggctttgat tgcagaagca gaagtggaca aggatattgt tgcaattcat    1500
gctgcaatgg gaggtggaac aggcttaaat ctcttccttc gccgtttccc aacaagatgc    1560
tttgatgttg aatagcgga acagcatgca gttacatttg ctgcaggatt agcctgtgaa    1620
ggccttaaac cattttgtgc aatctactca tctttcatgc agagggctta tgaccaggta    1680
gtccatgatg tggatttgca gaagctgcca gtaagatttg caatggacag agctggactg    1740
gttggagcag atggtcccac acattgtgga gcttttgatg tcactttat ggcatgtctc    1800 cctaacatgg ttgtgatggc tccttctgat gaggcagaac tttttcacat ggttgccacc    1860
gctgccgcca tagatgatcg tcctagctgc ttccgatatc caaggggtaa cggtgttggt    1920
gttcagctgc caccaggaaa caaaggcatt cctcttgagg ttggaaaagg caggatattg    1980
attgaagggg aaagagtggc actcttgggt tatgggacag cagttcagag ctgtttggct    2040
gctgcctctt tagtggaacc ccatggcttg cttataacag tagcagatgc gagattctgt    2100
aaacctttgg atcacaccct cattcgaagc ctagcaaaat cacatgaagt tttgataacg    2160
gttgaagaag gatcaattgg gggctttgga tctcatgttg cacattttct ggcccttgat    2220
ggtcttcttg atggcaaact gaagtggcgg ccactcgttc ttccagatag gtatattgac    2280
catggatccc cgtctgtcca gttgatagag gctggtctaa cgccatctca cgttgcagca    2340
acagtactca acatacttgg aaataaaaga gaagctctgc agataatgtc atcatagaga    2400
aagtggaaac ataacggttt tgcactttca acaatgtaaa atagaataat tgcaagattt    2460
attatgtcat catccatttg ngtatgaaat gtaattttag aatcactaca gaatcatgta    2520
acagcaccaa ctttggatag aattaataaa agtttcaact tttttttttt ttgttcaaaa    2580
aaaaaaaaaa a                                                          2591
```

<210> SEQ ID NO 2
<211> LENGTH: 720
<212> TYPE: PRT
<213> ORGANISM: Hevea brasiliensis

<400> SEQUENCE: 2

```
Met Ala Leu Ser Ala Cys Ser Phe Pro Ala His Val Asp Lys Ala Thr
 1               5                  10                  15

Ile Ser Asp Leu Gln Lys Tyr Gly Tyr Val Pro Ser Arg Ser Leu Trp
            20                  25                  30

Arg Thr Asp Leu Leu Ala Gln Ser Leu Gly Arg Leu Asn Gln Ala Lys
        35                  40                  45

Ser Lys Lys Gly Pro Gly Gly Ile Cys Ala Ser Leu Ser Glu Arg Gly
    50                  55                  60

Glu Tyr His Ser Gln Arg Pro Pro Thr Pro Leu Leu Asp Thr Thr Asn
65                  70                  75                  80

Tyr Pro Ile His Met Lys Asn Leu Ser Ile Lys Glu Leu Lys Gln Leu
                85                  90                  95

Ala Asp Glu Leu Arg Ser Asp Val Ile Phe Asn Val Ser Arg Thr Gly
            100                 105                 110

Gly His Leu Gly Ser Ser Leu Gly Val Val Glu Leu Thr Val Ala Leu
        115                 120                 125

His Tyr Val Phe Ser Ala Pro Arg Asp Lys Ile Leu Trp Asp Val Gly
    130                 135                 140

His Gln Ser Tyr Pro His Lys Ile Leu Thr Gly Arg Arg Glu Lys Met
145                 150                 155                 160
```

```
Tyr Thr Ile Arg Gln Thr Asn Gly Leu Ser Gly Phe Thr Lys Arg Ser
                165                 170                 175
Glu Ser Glu Tyr Asp Cys Phe Gly Thr His Ser Ser Thr Thr Ile
            180                 185                 190
Ser Ala Gly Leu Gly Met Ala Val Gly Arg Asp Leu Lys Gly Lys Lys
            195                 200                 205
Asn Asn Val Val Ala Val Ile Gly Asp Gly Ala Met Thr Ala Gly Gln
210                 215                 220
Ala Tyr Glu Ala Met Asn Asn Ala Gly Tyr Leu Asp Ser Asp Met Ile
225                 230                 235                 240
Val Ile Leu Asn Asp Asn Lys Gln Val Ser Leu Pro Thr Ala Thr Leu
                245                 250                 255
Asp Gly Pro Ile Pro Pro Val Gly Ala Leu Ser Ser Ala Leu Ser Arg
            260                 265                 270
Leu Gln Ser Asn Arg Pro Leu Arg Glu Leu Arg Glu Val Ala Lys Gly
            275                 280                 285
Val Thr Lys Gln Ile Gly Gly Pro Met His Glu Trp Ala Ala Lys Val
            290                 295                 300
Asp Glu Tyr Ala Arg Gly Met Ile Ser Gly Ser Gly Ser Thr Leu Phe
305                 310                 315                 320
Glu Glu Leu Gly Leu Tyr Tyr Ile Gly Pro Val Asp Gly His Asn Ile
                325                 330                 335
Asp Asp Leu Ile Ala Ile Leu Lys Glu Val Lys Ser Thr Lys Thr Thr
            340                 345                 350
Gly Pro Val Leu Ile His Val Val Thr Glu Lys Gly Arg Gly Tyr Pro
            355                 360                 365
Tyr Ala Glu Lys Ala Ala Asp Lys Tyr His Gly Val Thr Lys Phe Asp
            370                 375                 380
Pro Ala Thr Gly Lys Gln Phe Lys Gly Ser Ala Ile Thr Gln Ser Tyr
385                 390                 395                 400
Thr Thr Tyr Phe Ala Glu Ala Leu Ile Ala Glu Ala Glu Val Asp Lys
                405                 410                 415
Asp Ile Val Ala Ile His Ala Ala Met Gly Gly Gly Thr Gly Leu Asn
            420                 425                 430
Leu Phe Leu Arg Arg Phe Pro Thr Arg Cys Phe Asp Val Gly Ile Ala
            435                 440                 445
Glu Gln His Ala Val Thr Phe Ala Ala Gly Leu Ala Cys Glu Gly Leu
            450                 455                 460
Lys Pro Phe Cys Ala Ile Tyr Ser Ser Phe Met Gln Arg Ala Tyr Asp
465                 470                 475                 480
Gln Val Val His Asp Val Asp Leu Gln Lys Leu Pro Val Arg Phe Ala
                485                 490                 495
Met Asp Arg Ala Gly Leu Val Gly Ala Asp Gly Pro Thr His Cys Gly
            500                 505                 510
Ala Phe Asp Val Thr Phe Met Ala Cys Leu Pro Asn Met Val Val Met
            515                 520                 525
Ala Pro Ser Asp Glu Ala Glu Leu Phe His Met Val Ala Thr Ala Ala
            530                 535                 540
Ala Ile Asp Asp Arg Pro Ser Cys Phe Arg Tyr Pro Arg Gly Asn Gly
545                 550                 555                 560
Val Gly Val Gln Leu Pro Pro Gly Asn Lys Gly Ile Pro Leu Glu Val
                565                 570                 575
```

Gly Lys Gly Arg Ile Leu Ile Glu Gly Glu Arg Val Ala Leu Leu Gly
            580                 585                 590

Tyr Gly Thr Ala Val Gln Ser Cys Leu Ala Ala Ala Ser Leu Val Glu
        595                 600                 605

Pro His Gly Leu Leu Ile Thr Val Ala Asp Ala Arg Phe Cys Lys Pro
    610                 615                 620

Leu Asp His Thr Leu Ile Arg Ser Leu Ala Lys Ser His Glu Val Leu
625                 630                 635                 640

Ile Thr Val Glu Glu Gly Ser Ile Gly Gly Phe Gly Ser His Val Ala
                645                 650                 655

His Phe Leu Ala Leu Asp Gly Leu Leu Asp Gly Lys Leu Lys Trp Arg
            660                 665                 670

Pro Leu Val Leu Pro Asp Arg Tyr Ile Asp His Gly Ser Pro Ser Val
        675                 680                 685

Gln Leu Ile Glu Ala Gly Leu Thr Pro Ser His Val Ala Ala Thr Val
    690                 695                 700

Leu Asn Ile Leu Gly Asn Lys Arg Glu Ala Leu Gln Ile Met Ser Ser
705                 710                 715                 720

<210> SEQ ID NO 3
<211> LENGTH: 1929
<212> TYPE: DNA
<213> ORGANISM: Hevea brasiliensis

<400> SEQUENCE: 3
tttgggctaa agcttacacg actcactatg ggaattcctt agatttgaat accatcataa      60
ttatttattt aattttattt tagaatcaaa ataaaaaatt tattaacgta aaatattttt     120
gatatcatta aattaaaata atatactttt ataatcttac cctttccatt tattatggaa     180
atttcctaaa ataataaatt catttctggc attatatatt gtttctatct ccagcacctc     240
cctgcccact tatctttcct tcttctgcca ttttcacctg cttttacttt gctgcattcc     300
atggcgctca atttgctttc ccctgctgaa atcaaggcta tctccttctt agattccacc     360
aagtccagcc accttactaa gcttccaggt ggtttcagtt taaagaggaa ggattttggg     420
gcagcatttg ggaagaaagt gcagtgttcg gcccagcctc ctccaccagc ctggccagga     480
agagcttttc cagatttagg ccgtaagact tgggatggcc aaagcctat ttcagtcgtt      540
ggatccactg gctccattgg gactcagaca ttggacatcg tggcagagaa tccagataaa     600
ttcagagttg tggcactcgc agctggttca aatgttactc ttcttgcaga tcaggtgaag     660
actttcaaac ctcaacttgt tgctgttaga atgagtcat tagttcatga actcagagaa      720
gctttggctg atgttgaaga aaaacctgag attattcctg gggagcaagg agttgttgag     780
gttgctcgcc atccagatgc tgtcagtgta gttacaggaa tagtaggttg tgcaggctta     840
aagcctacgg tggctgcaat agaagctgga aaagacatat gcttggccaa taagagaca      900
ttaattgctg gagggccctt tgtccttcct cttgctcaca atataatgt gaaaattctc      960
ccggctgatt cagaacattc tgctatattt cagtgtattc aaggcctgcc agatggtgca    1020
ctgcggcgta ttatttaac tgcttcaggt ggagctttca gggattggcc tgttgataaa    1080
ttgaaagaag ttaaagtagc tgatgcttta agcatccta actggaatat ggggaaaaag     1140
attacagtgg actccgctac ccttttcaat aagggttag aagtcattga agcccattat      1200
ttgtttggag ctgagtatga ataattgag atagtaattc atccacaatc tataatacat     1260
tcaatggttg aaacacagga ttcatctgtt cttgcacagt tggggtggcc cgatatgcgt    1320

```
ttaccaattc tatatactat gtcatggcct gacagaatat actgctctga ataacctgg      1380 cctcgccttg acctttgcaa gcttgggtct ctaacattta agctcctga caatgtaaag     1440 taccttcta tggatcttgc ctatgctgct ggacgggctg gaggcaccat gactggagtg    1500
cttagtgctg cgaatgagaa agctgttgag atgttcatca atgaaaagat cggctatctt    1560
gatattttca agattgtgga gctaacgtgt gataaacata ggtcagaact ggtggcgtca    1620
ccctctctcg aggaaattat acattatgac ttgtgggcac gagactatgc tgctagtttg   1680
caacccactt ctggtctaag ccctgttctt gcatgattga ctgcctggaa ctacagagat   1740
tctcgatcct gccaagaaaa tggcgttctt cgtggggttt ttgggggca ttgtgtatca    1800 tataaatagc aagatgggca acccaaatgt gtttcccctt cattgcgtac cgattgtata   1860
attgctatcc ttgaacgctt gaaaaagtt gaagtggaga taaattttca gtgaaaaaaa    1920
aaaaaaaaa                                                            1929
```

<210> SEQ ID NO 4
<211> LENGTH: 471
<212> TYPE: PRT
<213> ORGANISM: Hevea brasiliensis

<400> SEQUENCE: 4

```
Met Ala Leu Asn Leu Leu Ser Pro Ala Glu Ile Lys Ala Ile Ser Phe
  1               5                  10                  15

Leu Asp Ser Thr Lys Ser Ser His Leu Thr Lys Leu Pro Gly Gly Phe
             20                  25                  30

Ser Leu Lys Arg Lys Asp Phe Gly Ala Ala Phe Gly Lys Lys Val Gln
         35                  40                  45

Cys Ser Ala Gln Pro Pro Pro Ala Trp Pro Gly Arg Ala Phe Pro
     50                  55                  60

Asp Leu Gly Arg Lys Thr Trp Asp Gly Pro Lys Pro Ile Ser Val Val
 65                  70                  75                  80

Gly Ser Thr Gly Ser Ile Gly Thr Gln Thr Leu Asp Ile Val Ala Glu
                 85                  90                  95

Asn Pro Asp Lys Phe Arg Val Val Ala Leu Ala Ala Gly Ser Asn Val
            100                 105                 110

Thr Leu Leu Ala Asp Gln Val Lys Thr Phe Lys Pro Gln Leu Val Ala
        115                 120                 125

Val Arg Asn Glu Ser Leu Val His Glu Leu Arg Glu Ala Leu Ala Asp
    130                 135                 140

Val Glu Glu Lys Pro Glu Ile Ile Pro Gly Glu Gln Gly Val Val Glu
145                 150                 155                 160

Val Ala Arg His Pro Asp Ala Val Ser Val Val Thr Gly Ile Val Gly
                165                 170                 175

Cys Ala Gly Leu Lys Pro Thr Val Ala Ala Ile Glu Ala Gly Lys Asp
            180                 185                 190

Ile Cys Leu Ala Asn Lys Glu Thr Leu Ile Ala Gly Gly Pro Phe Val
        195                 200                 205

Leu Pro Leu Ala His Lys Tyr Asn Val Lys Ile Leu Pro Ala Asp Ser
    210                 215                 220

Glu His Ser Ala Ile Phe Gln Cys Ile Gln Gly Leu Pro Asp Gly Ala
225                 230                 235                 240

Leu Arg Arg Ile Ile Leu Thr Ala Ser Gly Gly Ala Phe Arg Asp Trp
                245                 250                 255

Pro Val Asp Lys Leu Lys Glu Val Lys Val Ala Asp Ala Leu Lys His
```

```
                  260                 265                 270
Pro Asn Trp Asn Met Gly Lys Lys Ile Thr Val Asp Ser Ala Thr Leu
            275                 280                 285

Phe Asn Lys Gly Leu Glu Val Ile Glu Ala His Tyr Leu Phe Gly Ala
            290                 295                 300

Glu Tyr Asp Asn Ile Glu Ile Val Ile His Pro Gln Ser Ile Ile His
305                 310                 315                 320

Ser Met Val Glu Thr Gln Asp Ser Ser Val Leu Ala Gln Leu Gly Trp
                325                 330                 335

Pro Asp Met Arg Leu Pro Ile Leu Tyr Thr Met Ser Trp Pro Asp Arg
                340                 345                 350

Ile Tyr Cys Ser Glu Ile Thr Trp Pro Arg Leu Asp Leu Cys Lys Leu
            355                 360                 365

Gly Ser Leu Thr Phe Lys Ala Pro Asp Asn Val Lys Tyr Pro Ser Met
            370                 375                 380

Asp Leu Ala Tyr Ala Ala Gly Arg Ala Gly Thr Met Thr Gly Val
385                 390                 395                 400

Leu Ser Ala Ala Asn Glu Lys Ala Val Glu Met Phe Ile Asn Glu Lys
                405                 410                 415

Ile Gly Tyr Leu Asp Ile Phe Lys Ile Val Glu Leu Thr Cys Asp Lys
            420                 425                 430

His Arg Ser Glu Leu Val Ala Ser Pro Ser Leu Glu Glu Ile Ile His
            435                 440                 445

Tyr Asp Leu Trp Ala Arg Asp Tyr Ala Ala Ser Leu Gln Pro Thr Ser
450                 455                 460

Gly Leu Ser Pro Val Leu Ala
465                 470

<210> SEQ ID NO 5
<211> LENGTH: 1335
<212> TYPE: DNA
<213> ORGANISM: Hevea brasiliensis

<400> SEQUENCE: 5
gagaatacga ctcactatgg gaatccctta gattgaatca taaagggaaa tttaattaat      60
taatttattt taatttcaca tgagtgatgg gttagcacta gcagccactg gttctgctag     120
agctttgtct gcactcgatt cccattttc ctctttgctt tgttcaatag ggaaagaaa      180 ggaaggaaca gagaggaaga gggagagatc gagatgggtc atcatcttct tcacttgaac     240
cttacgatta tctctccttc tgcttctttc aaatcttcta attcattgtt tccatgtaat     300
catccccaaa ttcccaccaa ttcttttcac ttgccctccc tctcgaagtc atcagtccat     360
aaaatctctt ggatccaaaa gctgcccaga attgctactg ccactatcaa gtgctctgct     420
aagattgaaa atagctctgc agctgcgaaa gagaagagtg tttcggtcat tctgttggct     480
ggagggaagg gcaaaagaat gggtgcaagc atgccaaagc aatatctacc cctgttaggc     540
cagccaattg ctttatacag tttctacaca ttctcaaaaa tgaccgaagt gaaagaaatt     600
gttgtagtct gcgatccatc ctaccaagac attttgaag atgccaaaga aaatatcact     660
gtggacctca aatttgcact gcctgggaag gaaagacaag attctgtata caatggcctt     720
caggaagttg atttgaactc tgagcttgtt tgtgtccatg actcagctag acctctggtg     780
tcatctgcag aagtaaaaga ggtcctcaaa gatgcttgga taaacggagc agctgtgctt     840
ggtgttcctg ctaaagctac aattaaggag gcgaatagtg aatcttttgt agtgagaact     900
```

-continued

```
cttgaccgca aaacactttg ggaaatgcaa accccacagg tgattaagcc tgatttgctt    960
aaaaaaggct ttgagcttgt gaacagaggt ggtcttgaag tcactgatga tgtctccatc   1020
gtggagcacc ttaaacatcc cgtatacatt accgaaggat cttacacaaa catcaaggtc   1080
acaactccgg atgatatgtt acttgccgag agaattttga acttgaattc tggagaatct   1140
tcgaaatagg cttgtatttg attttttgcat tctattgttg ctccattcta tatctttcag   1200
aatgaaaaga caatatttc ttctctaatt ttaaagattt tgctgcattt gaggtctgat    1260
aaaaaaagac gatagcagat cttgcaataa taatattcta ttaggctcat cttcaaaccg   1320
aaaaaaaaaa aaaaa                                                    1335
```

<210> SEQ ID NO 6
<211> LENGTH: 311
<212> TYPE: PRT
<213> ORGANISM: Hevea brasiliensis

<400> SEQUENCE: 6

```
Met Gly His His Leu Leu His Leu Asn Leu Thr Ile Ile Ser Pro Ser
  1               5                  10                  15

Ala Ser Phe Lys Ser Ser Asn Ser Leu Phe Pro Cys Asn His Pro Gln
             20                  25                  30

Ile Pro Thr Asn Ser Phe His Leu Pro Ser Leu Ser Lys Ser Ser Val
         35                  40                  45

His Lys Ile Ser Trp Ile Gln Lys Leu Pro Arg Ile Ala Thr Ala Thr
     50                  55                  60

Ile Lys Cys Ser Ala Lys Ile Glu Asn Ser Ser Ala Ala Ala Lys Glu
 65                  70                  75                  80

Lys Ser Val Ser Val Ile Leu Leu Ala Gly Gly Lys Gly Lys Arg Met
                 85                  90                  95

Gly Ala Ser Met Pro Lys Gln Tyr Leu Pro Leu Leu Gly Gln Pro Ile
            100                 105                 110

Ala Leu Tyr Ser Phe Tyr Thr Phe Ser Lys Met Thr Glu Val Lys Glu
        115                 120                 125

Ile Val Val Val Cys Asp Pro Ser Tyr Gln Asp Ile Phe Glu Asp Ala
    130                 135                 140

Lys Glu Asn Ile Thr Val Asp Leu Lys Phe Ala Leu Pro Gly Lys Glu
145                 150                 155                 160

Arg Gln Asp Ser Val Tyr Asn Gly Leu Gln Glu Val Asp Leu Asn Ser
                165                 170                 175

Glu Leu Val Cys Val His Asp Ser Ala Arg Pro Leu Val Ser Ser Ala
            180                 185                 190

Glu Val Lys Glu Val Leu Lys Asp Ala Trp Ile Asn Gly Ala Ala Val
        195                 200                 205

Leu Gly Val Pro Ala Lys Ala Thr Ile Lys Glu Ala Asn Ser Glu Ser
    210                 215                 220

Phe Val Val Arg Thr Leu Asp Arg Lys Thr Leu Trp Glu Met Gln Thr
225                 230                 235                 240

Pro Gln Val Ile Lys Pro Asp Leu Leu Lys Lys Gly Phe Glu Leu Val
                245                 250                 255

Asn Arg Gly Gly Leu Glu Val Thr Asp Asp Val Ser Ile Val Glu His
            260                 265                 270

Leu Lys His Pro Val Tyr Ile Thr Glu Gly Ser Tyr Thr Asn Ile Lys
        275                 280                 285

Val Thr Thr Pro Asp Asp Met Leu Leu Ala Glu Arg Ile Leu Asn Leu
```

Asn Ser Gly Glu Ser Ser Lys
305             310

<210> SEQ ID NO 7
<211> LENGTH: 2069
<212> TYPE: DNA
<213> ORGANISM: Hevea brasiliensis

<400> SEQUENCE: 7

| | | | | |
|---|---|---|---|---|
| cagtttatac | gatcactatg | ggaattctta | agattaaatg tgggcgcttg ttactactta | 60 |
| gcggccacag | gttcagaatt | ttgtctgcac | ttaattccca ttctctcttt gctttgttct | 120 |
| ataaagccaa | agaacgggag | gaagagagag | aaagagagga atttggagtc tgggagagat | 180 |
| agagatgggc | catcatcttc | ttcgcatgaa | ccttacatct atcgcttctt ctgcttcttt | 240 |
| caaatcttct | aattcactgt | tccatgtaa | tcatcaccaa attccctcca attcttttca | 300 |
| cttgcccttt | cactctaaat | cctcaggcca | taaaatctct tggatccaaa agctgcccag | 360 |
| aattgtgact | atctctgtca | agtgctctgc | taagattgaa atagctctg cagctgtgaa | 420 |
| agagaagagt | gtttcggtca | ttctgttggc | tggaggaaag ggcaaaagaa tgggtgctag | 480 |
| catgccaaag | caatatctac | ccctgttagg | ccagccaatt gctttataca gtttctacac | 540 |
| attctcaaaa | atgattgaag | tgaaagaaat | tgttgtagtc tgcgatccat cctaccaaga | 600 |
| cattttgaa | gatgccaaag | aaaatatcaa | tgtggacctc aaattcgcac tgcctgggaa | 660 |
| ggaaagacag | gattctgtct | acagtggcct | tcaggaagtt gatttgaact ctgagcttgt | 720 |
| tgtgtccat | gactcagcta | gacctctggt | gtcatctgca gatgtaaaaa aggtcattga | 780 |
| cagtttatac | gatcactatg | ggaattctta | agattaaatg tgggcgcttg ttactactta | 840 |
| gcggccacag | gttcagaatt | ttgtctgcac | ttaattccca ttctctcttt gctttgttct | 900 |
| ataaagccaa | agaacgggag | gaagagagag | aaagagagga atttggagtc tgggagagat | 960 |
| agagatgggc | catcatcttc | ttcgcatgaa | ccttacatct atcgcttctt ctgcttcttt | 1020 |
| caaatcttct | aattcactgt | tccatgtaa | tcatcaccaa attccctcca attcttttca | 1080 |
| cttgcccttt | cactctaaat | cctcaggcca | taaaatctct tggatccaaa agctgcccag | 1140 |
| aattgtgact | atctctgtca | agtgctctgc | taagattgaa atagctctg cagctgtgaa | 1200 |
| agagaagagt | gtttcggtca | ttctgttggc | tggaggaaag ggcaaaagaa tgggtgctag | 1260 |
| catgccaaag | caatatctac | ccctgttagg | ccagccaatt gctttataca gtttctacac | 1320 |
| attctcaaaa | atgattgaag | tgaaagaaat | tgttgtagtc tgcgatccat cctaccaaga | 1380 |
| cattttgaa | gatgccaaag | aaaatatcaa | tgtggacctc aaattcgcac tgcctgggaa | 1440 |
| ggaaagacag | gattctgtct | acagtggcct | tcaggaagtt gatttgaact ctgagcttgt | 1500 |
| tgtgtccat | gactcagcta | gacctctggt | gtcatctgca gatgtaaaaa aggtcattga | 1560 |
| agatgcttgg | ataaatggag | cagctgtgct | tggtgttcct gctaaagcta caattaagga | 1620 |
| ggcaaacagt | gaatcttttg | tagtgagaac | tcttgaccgc aaaacacttt gggaaatgca | 1680 |
| aaccccacag | gtgattaagc | ctgatttgct | taaaaaaggc tttgagcttg tgagcagaga | 1740 |
| tggtcttgaa | gtcactgatg | atgtctctat | cgtggaacac cttaaacatc ccgtatacat | 1800 |
| tacagaagga | tcttacacga | acatcaaggt | cacgactcct gatgatttgt tgcttgctga | 1860 |
| gagaattttg | aacttgaatt | ctgaagaatc | ttcaaagtag gcttgttttt ggttttgca | 1920 |
| ttctattgtt | gctcatttct | atatcttcg | gaatgaaaag acaatatttt cttttctaat | 1980 | tttaaagatt ttgctgcatt tgaggtctga taaaagacga tagcagatct tgcaataata    2040 atattctatt aactcaaaaa aaaaaaaaa                                      2069

<210> SEQ ID NO 8
<211> LENGTH: 311
<212> TYPE: PRT
<213> ORGANISM: Hevea brasiliensis

<400> SEQUENCE: 8

Met Gly His His Leu Leu Arg Met Asn Leu Thr Ser Ile Ala Ser Ser
1               5                   10                  15

Ala Ser Phe Lys Ser Ser Asn Ser Leu Phe Pro Cys Asn His His Gln
            20                  25                  30

Ile Pro Ser Asn Ser Phe His Leu Pro Phe His Ser Lys Ser Ser Gly
        35                  40                  45

His Lys Ile Ser Trp Ile Gln Lys Leu Pro Arg Ile Val Thr Ile Ser
    50                  55                  60

Val Lys Cys Ser Ala Lys Ile Glu Asn Ser Ser Ala Ala Val Lys Glu
65                  70                  75                  80

Lys Ser Val Ser Val Ile Leu Leu Ala Gly Gly Lys Gly Lys Arg Met
                85                  90                  95

Gly Ala Ser Met Pro Lys Gln Tyr Leu Pro Leu Leu Gly Gln Pro Ile
            100                 105                 110

Ala Leu Tyr Ser Phe Tyr Thr Phe Ser Lys Met Ile Glu Val Lys Glu
        115                 120                 125

Ile Val Val Val Cys Asp Pro Ser Tyr Gln Asp Ile Phe Glu Asp Ala
    130                 135                 140

Lys Glu Asn Ile Asn Val Asp Leu Lys Phe Ala Leu Pro Gly Lys Glu
145                 150                 155                 160

Arg Gln Asp Ser Val Tyr Ser Gly Leu Gln Glu Val Asp Leu Asn Ser
                165                 170                 175

Glu Leu Val Cys Val His Asp Ser Ala Arg Pro Leu Val Ser Ser Ala
            180                 185                 190

Asp Val Lys Lys Val Ile Glu Asp Ala Trp Ile Asn Gly Ala Ala Val
        195                 200                 205

Leu Gly Val Pro Ala Lys Ala Thr Ile Lys Glu Ala Asn Ser Glu Ser
    210                 215                 220

Phe Val Val Arg Thr Leu Asp Arg Lys Thr Leu Trp Glu Met Gln Thr
225                 230                 235                 240

Pro Gln Val Ile Lys Pro Asp Leu Leu Lys Lys Gly Phe Glu Leu Val
                245                 250                 255

Ser Arg Asp Gly Leu Glu Val Thr Asp Val Ser Ile Val Glu His
            260                 265                 270

Leu Lys His Pro Val Tyr Ile Thr Glu Gly Ser Tyr Thr Asn Ile Lys
        275                 280                 285

Val Thr Thr Pro Asp Asp Leu Leu Ala Glu Arg Ile Leu Asn Leu
    290                 295                 300

Asn Ser Glu Glu Ser Ser Lys
305                 310

<210> SEQ ID NO 9
<211> LENGTH: 1512
<212> TYPE: DNA
<213> ORGANISM: Hevea brasiliensis

<400> SEQUENCE: 9

-continued

```
gaaagggaca atagtcccac aaaaggacaa ggaagtaaaa aaatcagctg atgaagattt      60
gataccattg tggctgttca aaattgactg caaaattgag ctagcagcca tggcttccgc     120
tcatttccac tgcaacaacc acgtcttcca ttattcctcc aattcattct ccaaaagcaa     180
tctaccttcg tttaggccta gtgggtctgt ctcttttat caaaagcaaa ggacttcatt     240
tgtcaaagcc tccaagaaac agctagagat agtgtatgat cctgaagaaa ggttaaacaa     300
gtgggcagat gaagtagaca agaatgctcc tctttcaagg ctcactttgt tctcgccttg     360
caagattaat attttcctta gaataaccga taagagagaa gatggatatc atgatttggc     420
atctctcttt catgtaatca gtctaggaga tacgattaag ttctctttat ctccttcgaa     480
atcgaaggac cgtttatcaa ccaatgtgtc tggcgtaccc cttgatgaaa ggaatttgat     540
tattaaagcc cttgacctat acaggaagaa aacaggcact gacaacttct tctggattca     600
tctagacaag agggtgccta ctggggcagg gcttggtggt ggaagcagta atgcagcaac     660
tgccctatgg gcagcaaatc agttcagtgg cggtcttgcc actgagaagg aactgctaga     720
atggtcaagt gagattggtt cagatatctc cttctttttt tctcgtggag cagcctattg     780
tactggtcgg ggtgaaattg ttcaagatat tcctacacca gttcctctcg accttccaat     840
ggttctcata aagccccagg aggcttgttc aactgctgaa gtttacaagc gctttcgatt     900
ggataaaacc agtcagattg atcctttaac attattggag aagatctcaa ggaatggaat     960
atctcaagat gtttgtatca atgatttgga acctcctgca tttgaagttc tcccatccct    1020
taaaagatta aaacagcgta taattgcagc cagccgtgga caatatgatg cagtttttat    1080
gtctgggagc ggaagtacca ttgttgggat tggttcacca gatcctccac aatttatata    1140
cgatgatgat gactcaaagg atgttttcgt gtcagaggca aacttcttga cccgtgaagc    1200
aaatcagtgg tacaaagaac ctgcttcaac tgctacttgt agttcccagt ccgatcgttc    1260
ccagtctatt gagtgacata tcttgtaaga aaaacgacat acatgaattt tttttaggat    1320
ttctcattaa tgttaattta tgccgcctgt agttttgtcc atcttaggaa taggttttta    1380
agttaaattt attgtcatga acaaataaga gcaattgctc aactcaaatc gtgtactagt    1440
tgcagtttca ctggcaaatt gttcactttg caaggtacat aaccttttga aagctcctga    1500
aaaaaaaaaa aa                                                        1512
```

<210> SEQ ID NO 10
<211> LENGTH: 388
<212> TYPE: PRT
<213> ORGANISM: Hevea brasiliensis

<400> SEQUENCE: 10

```
Met Ala Ser Ala His Phe His Cys Asn Asn His Val Phe His Tyr Ser
 1               5                   10                  15

Ser Asn Ser Phe Ser Lys Ser Asn Leu Pro Ser Phe Arg Pro Ser Gly
            20                  25                  30

Ser Val Ser Phe Tyr Gln Lys Gln Arg Thr Ser Phe Val Lys Ala Ser
        35                  40                  45

Lys Lys Gln Leu Glu Ile Val Tyr Asp Pro Glu Glu Arg Leu Asn Lys
    50                  55                  60

Trp Ala Asp Glu Val Asp Lys Asn Ala Pro Leu Ser Arg Leu Thr Leu
65                  70                  75                  80

Phe Ser Pro Cys Lys Ile Asn Ile Phe Leu Arg Ile Thr Asp Lys Arg
                85                  90                  95
```

```
Glu Asp Gly Tyr His Asp Leu Ala Ser Leu Phe His Val Ile Ser Leu
                100                 105                 110
Gly Asp Thr Ile Lys Phe Ser Leu Ser Pro Ser Lys Ser Lys Asp Arg
            115                 120                 125
Leu Ser Thr Asn Val Ser Gly Val Pro Leu Asp Glu Arg Asn Leu Ile
        130                 135                 140
Ile Lys Ala Leu Asp Leu Tyr Arg Lys Lys Thr Gly Thr Asp Asn Phe
145                 150                 155                 160
Phe Trp Ile His Leu Asp Lys Arg Val Pro Thr Gly Ala Gly Leu Gly
                165                 170                 175
Gly Gly Ser Ser Asn Ala Ala Thr Ala Leu Trp Ala Ala Asn Gln Phe
            180                 185                 190
Ser Gly Gly Leu Ala Thr Glu Lys Glu Leu Leu Glu Trp Ser Ser Glu
        195                 200                 205
Ile Gly Ser Asp Ile Ser Phe Phe Ser Arg Gly Ala Ala Tyr Cys
210                 215                 220
Thr Gly Arg Gly Glu Ile Val Gln Asp Ile Pro Thr Pro Val Pro Leu
225                 230                 235                 240
Asp Leu Pro Met Val Leu Ile Lys Pro Gln Glu Ala Cys Ser Thr Ala
                245                 250                 255
Glu Val Tyr Lys Arg Phe Arg Leu Asp Lys Thr Ser Gln Ile Asp Pro
            260                 265                 270
Leu Thr Leu Leu Glu Lys Ile Ser Arg Asn Gly Ile Ser Gln Asp Val
        275                 280                 285
Cys Ile Asn Asp Leu Glu Pro Pro Ala Phe Glu Val Leu Pro Ser Leu
290                 295                 300
Lys Arg Leu Lys Gln Arg Ile Ile Ala Ala Ser Arg Gly Gln Tyr Asp
305                 310                 315                 320
Ala Val Phe Met Ser Gly Ser Gly Ser Thr Ile Val Gly Ile Gly Ser
                325                 330                 335
Pro Asp Pro Pro Gln Phe Ile Tyr Asp Asp Asp Tyr Lys Asp Val
            340                 345                 350
Phe Val Ser Glu Ala Asn Phe Leu Thr Arg Glu Ala Asn Gln Trp Tyr
        355                 360                 365
Lys Glu Pro Ala Ser Thr Ala Thr Cys Ser Ser Gln Ser Asp Arg Ser
    370                 375                 380
Gln Ser Ile Glu
385

<210> SEQ ID NO 11
<211> LENGTH: 1036
<212> TYPE: DNA
<213> ORGANISM: Hevea brasiliensis

<400> SEQUENCE: 11
atgaactcaa tggctatggc cactcacttg tacacctcct attctccaat cacctccaag     60
accatcacca ctaattacaa cagcaacaag gctctttctg tccctttaca taaatcgata    120
gcctcgcctt ctctttctct gagaacaacg gccagacttt ccatatcagc agctgcagga    180
gctactgctt tgcaagtgga tggacccccc acgtctagta aaggaccaaa gtctttgcct    240
tttagagtgg gtcatgggtt cgatctccat cgtttagagc tgggtacccc tttgatcatt    300
ggtgggatta atatcccaca tgaaagaggc tgtgaggctc actctgatgg agacgtgtta    360
ttgcattgtg tagtcgatgc aatattaggt gcattggggc tgcctgatat tgggcagata    420
```

```
ttcccagatt ctgatcccaa gtggaaggga gctccatcat ctgttttat taaagaagct    480 gtaagactca tgcatgaggc aggctatgat attggaaact tggatgccac cttgattctt    540
caaagaccaa aactgagccc ccacaaggag gttatcaggg acaatttgtg tcagctgctc    600
ggagcagatc cttctgtaat aaatctgaag gcaaaaactc atgagaaggt tgacagctta    660
ggtgaaaata gaagtattgc agctcataca gtggttcttc tcatgaagaa gtaaagtagt    720
tctttaaaaa ctaaaaaatt tggagttagc cattgtactt ggttagcgtt gttgtcactg    780
ttacagagat gaacatatgc tggttctttt gaagacccat ctcacactag aacaatttca    840
tgatgcaagt tgacttaatg tcagtttcta ccacacttga aagaatagta tcttgtccct    900
gatatgttgt tatgatgcct gtatttataa gtccatttta tttggggcat ttgtcttgga    960
attatgtaca ataaacatct gaaaacgaag catagttctt gaaacgatag ttcttggaca   1020
aacaaaaaaa aaaaaa                                                    1036
```

<210> SEQ ID NO 12
<211> LENGTH: 237
<212> TYPE: PRT
<213> ORGANISM: Hevea brasiliensis

<400> SEQUENCE: 12

```
Met Asn Ser Met Ala Met Ala Thr His Leu Tyr Thr Ser Tyr Ser Pro
  1               5                  10                  15

Ile Thr Ser Lys Thr Ile Thr Thr Asn Tyr Asn Ser Asn Lys Ala Leu
             20                  25                  30

Ser Val Pro Leu His Lys Ser Ile Ala Ser Pro Ser Leu Ser Leu Arg
         35                  40                  45

Thr Thr Ala Arg Leu Ser Ile Ser Ala Ala Gly Ala Thr Ala Leu
     50                  55                  60

Gln Val Asp Gly Pro Pro Thr Ser Ser Lys Gly Pro Lys Ser Leu Pro
 65                  70                  75                  80

Phe Arg Val Gly His Gly Phe Asp Leu His Arg Leu Glu Pro Gly Tyr
                 85                  90                  95

Pro Leu Ile Ile Gly Gly Ile Asn Ile Pro His Glu Arg Gly Cys Glu
            100                 105                 110

Ala His Ser Asp Gly Asp Val Leu Leu His Cys Val Asp Ala Ile
        115                 120                 125

Leu Gly Ala Leu Gly Leu Pro Asp Ile Gly Gln Ile Phe Pro Asp Ser
    130                 135                 140

Asp Pro Lys Trp Lys Gly Ala Pro Ser Ser Val Phe Ile Lys Glu Ala
145                 150                 155                 160

Val Arg Leu Met His Glu Ala Gly Tyr Asp Ile Gly Asn Leu Asp Ala
                165                 170                 175

Thr Leu Ile Leu Gln Arg Pro Lys Leu Ser Pro His Lys Glu Val Ile
            180                 185                 190

Arg Asp Asn Leu Cys Gln Leu Leu Gly Ala Asp Pro Ser Val Ile Asn
        195                 200                 205

Leu Lys Ala Lys Thr His Glu Lys Val Asp Ser Leu Gly Glu Asn Arg
    210                 215                 220

Ser Ile Ala Ala His Thr Val Val Leu Leu Met Lys Lys
225                 230                 235
```

<210> SEQ ID NO 13
<211> LENGTH: 989
<212> TYPE: DNA

<213> ORGANISM: Hevea brasiliensis

<400> SEQUENCE: 13

```
tagagagaag taaacacaag cacacaaaaa acagagtttt ttctgcgaat gaactcaatg      60
gctatggcca ctcacttgta cacctcttat tctccaatca ccaccaagac catctcctct     120
aacaataaca gcgacaaggt tctttctctt cctttacagc caaggcatgc tatatcgata     180
gcctcaccat ctctttctct gagaacaacg accagatttt ccatatcagc agctgcagga     240
accactgctg tgcaagtcga tggacctacc acttctaata aaggaccaaa gtctttgcct     300
tttagagtgg gtcatgggtt cgatctccac cgtttagagc ctgggtaccc tttgatcatt     360
ggtgggatta atatcccgca tgaaagaggc tgtgaggctc actctgatgg agacgtgtta     420
ttgcactgtg ttgtggatgc aatattgggt gcattgggc tgcctgacat tgggcagata     480
ttcccagatt ctgatcccaa gtggaaggga gctccatcgt ctgttttcat taagaagct     540
gtaagactca tgcatgaggc tggctatgat attggaaact tggatgccac cttaattctt     600
caaagaccaa aactgagccc ccacaaggag gcgatcagag acaatttgtg tcagctgctt     660
ggagcagatc cttctgttat aaatctgaaa gcaaaaactc atgagaaggt tgacagctta     720
ggtgaaaata gaagtattgc agctcacaca gtggttcttc tcatgaagaa gtaaaggata     780
tcttaaaaaa ctcaaatatt tggaatttaa ctgttgtact tcgttagcat tgttgccact     840
gttacagaga ttaacaagtt ggttcttgtg acgatccatt ttacactata acagtttctt     900
aaagttggtt tctaccatac ctgaaagaat aatatcttgt ccatgatatg ttgttacaat     960
acttgtatttt gtccaaaaaa aaaaaaaaa                                     989
```

<210> SEQ ID NO 14
<211> LENGTH: 241
<212> TYPE: PRT
<213> ORGANISM: Hevea brasiliensis

<400> SEQUENCE: 14

```
Met Asn Ser Met Ala Met Ala Thr His Leu Tyr Thr Ser Tyr Ser Pro
  1               5                  10                  15

Ile Thr Thr Lys Thr Ile Ser Ser Asn Asn Ser Asp Lys Val Leu
             20                  25                  30

Ser Leu Pro Leu Gln Pro Arg His Ala Ile Ser Ile Ala Ser Pro Ser
         35                  40                  45

Leu Ser Leu Arg Thr Thr Thr Arg Phe Ser Ile Ser Ala Ala Ala Gly
     50                  55                  60

Thr Thr Ala Val Gln Val Asp Gly Pro Thr Thr Ser Asn Lys Gly Pro
 65                  70                  75                  80

Lys Ser Leu Pro Phe Arg Val Gly His Gly Phe Asp Leu His Arg Leu
                 85                  90                  95

Glu Pro Gly Tyr Pro Leu Ile Ile Gly Gly Ile Asn Ile Pro His Glu
            100                 105                 110

Arg Gly Cys Glu Ala His Ser Asp Gly Asp Val Leu Leu His Cys Val
        115                 120                 125

Val Asp Ala Ile Leu Gly Ala Leu Gly Leu Pro Asp Ile Gly Gln Ile
    130                 135                 140

Phe Pro Asp Ser Asp Pro Lys Trp Lys Gly Ala Pro Ser Ser Val Phe
145                 150                 155                 160

Ile Lys Glu Ala Val Arg Leu Met His Glu Ala Gly Tyr Asp Ile Gly
                165                 170                 175
```

Asn Leu Asp Ala Thr Leu Ile Leu Gln Arg Pro Lys Leu Ser Pro His
            180                 185                 190

Lys Glu Ala Ile Arg Asp Asn Leu Cys Gln Leu Leu Gly Ala Asp Pro
        195                 200                 205

Ser Val Ile Asn Leu Lys Ala Lys Thr His Glu Lys Val Asp Ser Leu
    210                 215                 220

Gly Glu Asn Arg Ser Ile Ala Ala His Thr Val Val Leu Leu Met Lys
225                 230                 235                 240

Lys

<210> SEQ ID NO 15
<211> LENGTH: 2745
<212> TYPE: DNA
<213> ORGANISM: Hevea brasiliensis

<400> SEQUENCE: 15

| | | | | |
|---|---|---|---|---|
| tgtttataga | ccatataggg | aattcttaga | tttgagatca | tcacccggca | cacggcccct | 60 |
| tctctctctc | aatctcttta | ttgctaccac | tacttcttca | tttcgctccc | cagatccttc | 120 |
| gtcttcacta | tcactcttca | attctctttc | tttccaggtg | agaaagtttg | attgtaggtg | 180 |
| gaaatggcga | ctggagctgt | gccggcgtcg | tttactggtc | ttaagaccag | ggactccagc | 240 |
| ttaggatttg | gcaagagcat | ggattttgtg | agagtttgtg | atttgaagag | gatcaaatct | 300 |
| ggtaggaaaa | aaatttctat | gattcgaaac | tcgaatcctg | tcctgagat | ggttgaactt | 360 |
| cagcccgcgt | cagaagggag | ccctttgtta | gttcctagac | aaaagtattg | tgaatctgtt | 420 |
| cacaagactg | tcaggaggaa | aacaagaacc | gtaatggtcg | gaaatgtggc | tcttggtagt | 480 |
| gagcatccta | tcagggttca | aactatgact | acaagtgaca | ctaaggatgt | tgctgggaca | 540 |
| gttgaacagg | taatgagaat | agcagacaag | ggggcagatt | tggttcggat | aacagttcaa | 600 |
| gggaaaagag | aagcagatgc | ttgctttgaa | ataaaaaatt | ctcttgtgca | gaaaaattac | 660 |
| aatatacctt | tggtcgcaga | tattcacttt | gctccatctg | ttgcattgcg | agtagctgaa | 720 |
| tgttttgaca | aaattcgtgt | aaatccagga | aattttgctg | ataggcgggc | tcagtttgag | 780 |
| aagctcgagt | acacagaaga | tgactatcag | aaagaactcg | agcatatcga | gcaggttttt | 840 |
| actccattgg | ttgaaaaatg | taagaagtat | ggaagggcaa | tgcgcattgg | aacaaaccat | 900 |
| ggaagtcttt | cagatcgtat | aatgagctac | atgagagatt | cacctagggg | aatggttgaa | 960 |
| tctgcatttg | agtttgcaag | aatatgccgg | aaattggact | tccataattt | tgtattttca | 1020 |
| atgaaagcta | gcaatccagt | catcatggtc | caggcatacc | gtcttcttgt | agcagaaatg | 1080 |
| tatgttcagg | gctgggatta | tccattacac | ttgggtgtca | ctgaagctgg | agaaggagaa | 1140 |
| gatgggcgta | tgaaatctgc | aattggcatt | gggactcttc | ttcaggatgg | tttgggtgat | 1200 |
| acaatcaggg | tatcactgac | agaaccacca | gagaaggaga | ttgatccttg | cagaaggttg | 1260 |
| gccaaccttg | gtatgagagc | ttctacagtt | caacaaggag | tggcaccatt | tgaagaaaag | 1320 |
| cataggcatt | attttgattt | ccagcgccga | tccggccaat | gccagtaca | aaaggagggt | 1380 |
| gaagaggtgg | attatagagg | tgtcctgcac | cgtgatggct | ccgttctcat | gtcggtttcc | 1440 |
| ttagatcagt | tgaaggcacc | tgaactccta | tacaagtcac | ttgcagcaaa | gcttgttgtt | 1500 |
| ggaatgcctt | ttaaggacct | ggcaacagtt | gactcaatcc | tgttgggaga | gcttccacct | 1560 |
| gtggaggata | tgatgctcg | gctagctctc | aaaagactga | tagatatcag | catgggagta | 1620 |
| attgttcctt | tgtcagaaca | gctgacaaag | ccattaccca | atgccacggt | tcttgtaaat | 1680 |
| cttaaggagt | tgtcaactgg | tgctcacaag | cttttgccag | aaggtacacg | cttagttgtg | 1740 |

-continued

```
tctgcacgtg gtgatgagcc ttatgaagaa ctggaaatcc tcaaagacat agatgctaca    1800
atgattcttc atgatctacc atttacagaa gacaaaattg gtagagtgca tgcagcaagg    1860
aggttatttg agtttctatc agacaatgct ctgaacttcc ctgtaattca ccatattcaa    1920
ttttcaaatg caattcacag ggatgacttg gtcattggcg ctggtacaaa tgctggggct    1980
cctttagtag atggtcttgg agatggtatc ctgctagaag ccccagacca ggactttgat    2040
tttctgagga atacctcttt caacttgcta cagggttgca gaatgagaaa tacaaagacg    2100
gagtacgtct catgtccatc ctgtgggaga actttgtttg accttcaaga tataagtgca    2160
gaaattcgag aaaagacctc tcacttgcct ggtgtctcga tcgcaattat gggttgcatt    2220
gtaaatgggc caggggagat ggctgatgca gatttttgggt atgttggtgg tgctcctgga    2280
aagattgacc tatatgttgg aaagactgtg gtaaagcgtg gaattgcaat ggagggagct    2340
accgatgcat tgatccagct aatcaaagat catggccgct gggtcgatcc tcctgcagaa    2400
gagtaataat atcaagtaat tctaatttgg atataggaag aaagtggcag taaaagggac    2460
ttcacagttt acatattcta ttatacatgt aatgcaaaag ccagaagttg aaatcttaga    2520
gagtctagct gcaccgtgta gaaatctttc cttgtatgtg aacgtcggtg taattggaat    2580
gtaatcttca attagcatgc aaataacttt gtaattctct caccaataag aaattcaaga    2640
tttcctgaat gttgcaaatt gtagatcaac caatgtacgc agacatacca attaaattga    2700
attccaacaa tatagaattt gagcttttgc aaaaaaaaaa aaaaa                    2745
```

<210> SEQ ID NO 16
<211> LENGTH: 740
<212> TYPE: PRT
<213> ORGANISM: Hevea brasiliensis

<400> SEQUENCE: 16

```
Met Ala Thr Gly Ala Val Pro Ala Ser Phe Thr Gly Leu Lys Thr Arg
  1               5                  10                  15

Asp Ser Ser Leu Gly Phe Gly Lys Ser Met Asp Phe Val Arg Val Cys
             20                  25                  30

Asp Leu Lys Arg Ile Lys Ser Gly Arg Lys Ile Ser Met Ile Arg
         35                  40                  45

Asn Ser Asn Pro Gly Pro Glu Met Val Glu Leu Gln Pro Ala Ser Glu
     50                  55                  60

Gly Ser Pro Leu Leu Val Pro Arg Gln Lys Tyr Cys Glu Ser Val His
 65                  70                  75                  80

Lys Thr Val Arg Arg Lys Thr Arg Thr Val Met Val Gly Asn Val Ala
                 85                  90                  95

Leu Gly Ser Glu His Pro Ile Arg Val Gln Thr Met Thr Thr Ser Asp
            100                 105                 110

Thr Lys Asp Val Ala Gly Thr Val Glu Gln Val Met Arg Ile Ala Asp
        115                 120                 125

Lys Gly Ala Asp Leu Val Arg Ile Thr Val Gln Gly Lys Arg Glu Ala
    130                 135                 140

Asp Ala Cys Phe Glu Ile Lys Asn Ser Leu Val Gln Lys Asn Tyr Asn
145                 150                 155                 160

Ile Pro Leu Val Ala Asp Ile His Phe Ala Pro Ser Val Ala Leu Arg
                165                 170                 175

Val Ala Glu Cys Phe Asp Lys Ile Arg Val Asn Pro Gly Asn Phe Ala
            180                 185                 190
```

```
Asp Arg Arg Ala Gln Phe Glu Lys Leu Glu Tyr Thr Glu Asp Asp Tyr
            195                 200                 205

Gln Lys Glu Leu Glu His Ile Glu Gln Val Phe Thr Pro Leu Val Glu
210                 215                 220

Lys Cys Lys Lys Tyr Gly Arg Ala Met Arg Ile Gly Thr Asn His Gly
225                 230                 235                 240

Ser Leu Ser Asp Arg Ile Met Ser Tyr Tyr Gly Asp Ser Pro Arg Gly
            245                 250                 255

Met Val Glu Ser Ala Phe Glu Phe Ala Arg Ile Cys Arg Lys Leu Asp
                260                 265                 270

Phe His Asn Phe Val Phe Ser Met Lys Ala Ser Asn Pro Val Ile Met
            275                 280                 285

Val Gln Ala Tyr Arg Leu Leu Val Ala Glu Met Tyr Val Gln Gly Trp
290                 295                 300

Asp Tyr Pro Leu His Leu Gly Val Thr Glu Ala Gly Glu Gly Glu Asp
305                 310                 315                 320

Gly Arg Met Lys Ser Ala Ile Gly Ile Gly Thr Leu Leu Gln Asp Gly
                325                 330                 335

Leu Gly Asp Thr Ile Arg Val Ser Leu Thr Glu Pro Pro Glu Lys Glu
            340                 345                 350

Ile Asp Pro Cys Arg Arg Leu Ala Asn Leu Gly Met Arg Ala Ser Thr
            355                 360                 365

Val Gln Gln Gly Val Ala Pro Phe Glu Glu Lys His Arg His Tyr Phe
370                 375                 380

Asp Phe Gln Arg Arg Ser Gly Gln Leu Pro Val Gln Lys Glu Gly Glu
385                 390                 395                 400

Glu Val Asp Tyr Arg Gly Val Leu His Arg Asp Gly Ser Val Leu Met
                405                 410                 415

Ser Val Ser Leu Asp Gln Leu Lys Ala Pro Glu Leu Leu Tyr Lys Ser
            420                 425                 430

Leu Ala Ala Lys Leu Val Val Gly Met Pro Phe Lys Asp Leu Ala Thr
            435                 440                 445

Val Asp Ser Ile Leu Leu Gly Glu Leu Pro Pro Val Glu Asp Asn Asp
450                 455                 460

Ala Arg Leu Ala Leu Lys Arg Leu Ile Asp Ile Ser Met Gly Val Ile
465                 470                 475                 480

Val Pro Leu Ser Glu Gln Leu Thr Lys Pro Leu Pro Asn Ala Thr Val
                485                 490                 495

Leu Val Asn Leu Lys Glu Leu Ser Thr Gly Ala His Lys Leu Leu Pro
            500                 505                 510

Glu Gly Thr Arg Leu Val Val Ser Ala Arg Gly Asp Glu Pro Tyr Glu
            515                 520                 525

Glu Leu Glu Ile Leu Lys Asp Ile Asp Ala Thr Met Ile Leu His Asp
530                 535                 540

Leu Pro Phe Thr Glu Asp Lys Ile Gly Arg Val His Ala Ala Arg Arg
545                 550                 555                 560

Leu Phe Glu Phe Leu Ser Asp Asn Ala Leu Asn Phe Pro Val Ile His
                565                 570                 575

His Ile Gln Phe Ser Asn Ala Ile His Arg Asp Leu Val Ile Gly
            580                 585                 590

Ala Gly Thr Asn Ala Gly Ala Pro Leu Val Asp Gly Leu Gly Asp Gly
            595                 600                 605

Ile Leu Leu Glu Ala Pro Asp Gln Asp Phe Asp Phe Leu Arg Asn Thr
```

```
                610             615             620
Ser Phe Asn Leu Leu Gln Gly Cys Arg Met Arg Asn Thr Lys Thr Glu
625                 630                 635                 640

Tyr Val Ser Cys Pro Ser Cys Gly Arg Thr Leu Phe Asp Leu Gln Asp
                645                 650                 655

Ile Ser Ala Glu Ile Arg Glu Lys Thr Ser His Leu Pro Gly Val Ser
            660                 665                 670

Ile Ala Ile Met Gly Cys Ile Val Asn Gly Pro Gly Glu Met Ala Asp
                675                 680                 685

Ala Asp Phe Gly Tyr Val Gly Gly Ala Pro Gly Lys Ile Asp Leu Tyr
            690                 695                 700

Val Gly Lys Thr Val Val Lys Arg Gly Ile Ala Met Glu Gly Ala Thr
705                 710                 715                 720

Asp Ala Leu Ile Gln Leu Ile Lys Asp His Gly Arg Trp Val Asp Pro
                725                 730                 735

Pro Ala Glu Glu
            740

<210> SEQ ID NO 17
<211> LENGTH: 1682
<212> TYPE: DNA
<213> ORGANISM: Hevea brasiliensis

<400> SEQUENCE: 17
aagagggaag agaaggacga ttatagactc actatgggaa ttcttagatt tggggtcacc      60
gccactgctt ctgctagctc aacgctttcg cttttctctc tctgccatgg ctgtctctct     120
gcaactctgc cgcgtctccc tccgcagcga tctcttctcc cgtgagaatc tcgctcctct     180
taatcgcagg aagtttctat ctgttcgatg cgctgctggt ggcgatgagt catctgctgg     240
ttctgtcgct gtggaatccg attttgacgc taaggttttt agacataact gacgcgaag      300
caagaattat aatcggagag ttttggaca caaggaagag actcttgagc tcatgaacca     360
agagtatacc agtgatatca taaagacttt gaaggaaaat ggcaatcagt acaaatgggg     420
aaatgttacc attaaactgg cagaagctta tgggttttgc tggggagttg agcgggcggt     480
ccagattgct tatgaagcta ggaaacagtt tcctgacgag aagatttgga ttaccaatga     540
gattattcac aacccaactg ttaataagcg tttagaagag atgaatgtcc aaaatattcc     600
tgttggcgaa ggaaagaaac actttgaagt gtggacagt ggtgatgttg tgattttgcc      660
tgcttttggg gctgctgtgg aggagatgtt gaccttgagc aacaaaaatg tgcaaattgt     720
tgacacaact tgcccttggg tatccaaggt ttggaatact gttgagaagc acaagaaggg     780
agagtacact tcaatcattc acggtaaata ttctcatgag gaaaccatag ctactgcctc     840
ttttgctgga aagcatatca ttgtgaagaa tatggaagag gcaatgtatg tgtgtgatta     900
cattcttggt ggtcaactta tggatctag ctcaacaaaa gaggcatttc tagagaaatt      960
taaatatgca gttctaagg gatttgatcc agatgttgac ctggataagg ttggtattgc     1020
aaatcaaacc acaatgctta agggagaaac agaagagatt gggaaattgg tggagaagac     1080
catgatgcgt aaatatggag tggaaaaatgt taatgaccac tttatcagct ttaacaccat     1140
tgtgatgct actcaagaac gacaagatgc tatgtttaag ttggtggagg agaagttga      1200
tcttattta gtagtggtg gctggaactc aagcaacacc tcacacctcc aagaaattgc     1260
tgagcttcgt ggaattcctt catattggat tgacagtgaa cagaggattg gtccaggaaa     1320
caaaatagct tataagttga atcacgggga gttggttgag aaggagaact tcctaccaga     1380
```

```
aggtcccatt acaattggca taacatctgg tgcctctact cctgataagg ttgttgaaga    1440
tgtccttgtc aaggtgttcg acatcaagcg tgacgaagct ttgcaagtag cataaatgta    1500
ccttttagtg catcatcaac aatggcagta agactatata actgagtgta tcattaacaa    1560
gaaaggctct gcaagatctc cgatatacca ttccttgtac tcaaattcat aatgttggta    1620
atatagagat tgtggtagag ctgcaattag tggttggata ttttgactgc aaaaaaaaaa    1680
aa                                                                   1682

<210> SEQ ID NO 18
<211> LENGTH: 462
<212> TYPE: PRT
<213> ORGANISM: Hevea brasiliensis

<400> SEQUENCE: 18

Met Ala Val Ser Leu Gln Leu Cys Arg Val Ser Leu Arg Ser Asp Leu
  1               5                  10                  15

Phe Ser Arg Glu Asn Leu Ala Pro Leu Asn Arg Arg Lys Phe Leu Ser
                 20                  25                  30

Val Arg Cys Ala Ala Gly Gly Asp Glu Ser Ser Ala Gly Ser Val Ala
             35                  40                  45

Val Glu Ser Asp Phe Asp Ala Lys Val Phe Arg His Asn Leu Thr Arg
 50                  55                  60

Ser Lys Asn Tyr Asn Arg Arg Gly Phe Gly His Lys Glu Glu Thr Leu
 65                  70                  75                  80

Glu Leu Met Asn Gln Glu Tyr Thr Ser Asp Ile Ile Lys Thr Leu Lys
                 85                  90                  95

Glu Asn Gly Asn Gln Tyr Lys Trp Gly Asn Val Thr Ile Lys Leu Ala
            100                 105                 110

Glu Ala Tyr Gly Phe Cys Trp Gly Val Glu Arg Ala Val Gln Ile Ala
            115                 120                 125

Tyr Glu Ala Arg Lys Gln Phe Pro Asp Glu Lys Ile Trp Ile Thr Asn
130                 135                 140

Glu Ile Ile His Asn Pro Thr Val Asn Lys Arg Leu Glu Glu Met Asn
145                 150                 155                 160

Val Gln Asn Ile Pro Val Gly Glu Gly Lys Lys His Phe Glu Val Val
                165                 170                 175

Asp Ser Gly Asp Val Val Ile Leu Pro Ala Phe Gly Ala Ala Val Glu
            180                 185                 190

Glu Met Leu Thr Leu Ser Asn Lys Asn Val Gln Ile Val Asp Thr Thr
            195                 200                 205

Cys Pro Trp Val Ser Lys Val Trp Asn Thr Val Glu Lys His Lys Lys
    210                 215                 220

Gly Glu Tyr Thr Ser Ile Ile His Gly Lys Tyr Ser His Glu Glu Thr
225                 230                 235                 240

Ile Ala Thr Ala Ser Phe Ala Gly Lys His Ile Ile Val Lys Asn Met
                245                 250                 255

Glu Glu Ala Met Tyr Val Cys Asp Tyr Ile Leu Gly Gly Gln Leu Asn
            260                 265                 270

Gly Ser Ser Thr Lys Glu Ala Phe Leu Glu Lys Phe Lys Tyr Ala
            275                 280                 285

Val Ser Lys Gly Phe Asp Pro Asp Val Asp Leu Asp Lys Val Gly Ile
        290                 295                 300

Ala Asn Gln Thr Thr Met Leu Lys Gly Glu Thr Glu Glu Ile Gly Lys
305                 310                 315                 320
```

```
Leu Val Glu Lys Thr Met Met Arg Lys Tyr Gly Val Glu Asn Val Asn
                325             330             335
Asp His Phe Ile Ser Phe Asn Thr Ile Cys Asp Ala Thr Gln Glu Arg
            340             345             350
Gln Asp Ala Met Phe Lys Leu Val Glu Glu Lys Leu Asp Leu Ile Leu
        355             360             365
Val Val Gly Gly Trp Asn Ser Ser Asn Thr Ser His Leu Gln Glu Ile
    370             375             380
Ala Glu Leu Arg Gly Ile Pro Ser Tyr Trp Ile Asp Ser Glu Gln Arg
385             390             395             400
Ile Gly Pro Gly Asn Lys Ile Ala Tyr Lys Leu Asn His Gly Glu Leu
            405             410             415
Val Glu Lys Glu Asn Phe Leu Pro Glu Gly Pro Ile Thr Ile Gly Ile
        420             425             430
Thr Ser Gly Ala Ser Thr Pro Asp Lys Val Val Glu Asp Val Leu Val
        435             440             445
Lys Val Phe Asp Ile Lys Arg Asp Glu Ala Leu Gln Val Ala
    450             455             460
```

GENE CLUSTER INVOLVED IN BIOSYNTHESIS OF ISOPENTENYL DIPHOSPHATE IN THE NON-MEVALONATE PATHWAY OF *HEVEA BRASILIENSIS*

This is a divisional of application Ser. No. 11/522,391 (filed Sep. 18, 2006), which claims priority to JP 2005-270066 (filed Sep. 16, 2005) and JP 2006-238822 (filed Sep. 4, 2006), the entire disclosures of which are hereby incorporated by reference.

BACKGROUND OF THE INVENTION

1. Field of the Invention

The present invention relates to a gene cluster involved in biosynthesis of isopentenyl diphosphate in the non-mevalonate pathway of *Hevea brasiliensis*.

2. Background Art

All kinds of steroids, terpenoids, carotinoids, and all kinds of vitamins are composed of plural 5-carbon isoprenes covalently bound to one another. The basic isoprene structure is called "isoprene unit", and a compound having isoprene unit is generically called "isoprenoid". Isopentenyl diphosphate (IPP), a compound having five-carbons, serves as a unit in condensation reaction when an isoprenoid compound is synthesized. The two pathways of mevalonate pathway and the non-mevalonate pathway are known as the IPP biosynthesis pathways. In plants, it is said that the mevalonate pathway functions in cell cytoplasm and the non-mevalonate pathway functions in plastids. In *Escherichia coli*, each of the non-mevalonate pathway genes is isolated, and its functions are confirmed. In *Hevea brasiliensis*, on the other hand, the sequences of the gene cluster have not been reported. FIG. 1 shows the non-mevalonate pathway of IPP synthesis. Details about isoprenoid biosynthesis by the non-mevalonate pathway are given in the general remarks in W. Eisenreich et al., Cell Mol. Life Sci. 61 (2004) 1401-1426, for example.

In the non-mevalonate pathway, firstly glyceraldehyde 3-phosphate and pyruvic acid are catalyzed by 1-deoxy-D-xylulose 5-phosphate synthase (DXS) to undergo condensation accompanied by decarboxylation reaction, thereby 1-deoxy-D-xylulose 5-phosphate (DXP) is formed. DXS catalyzes transfer of 2 carbonates using thiamine diphosphate as a cofactor by the reaction mechanism similar to transketolase and pyruvic acid decarboxylase.

DXP undergoes transferring reaction and then reduced through catalysis by 1-deoxy-D-xylulose 5-phosphate reductoisomerase (DXR), thereby forms 2-C-methyl-D-erythritol-4-phosphate (MEP). MEP is conjugated with CDP by MEP cytidyltransferase (MCT) to form 4-(cytidine-5'-diphospho)-2-C-methyl-D-erythritol (MEPPC). The 3-Hydroxyl group of MEPPC is phosphorylated by 4-(cytidine-5'-diphospho)-2-C-methyl-D-erythritol kinase (CMK), and MEPPC is converted to 4-(cytidine-5'-diphospho)-2-C-methyl-D-erythritol 2-phosphate (MEPPCP).

MEPPCP is catalyzed by 2-C-methylerythritol 2,4-cyclodiphosphate synthase (MECPS) to form 2-C-methylerythritol 2,4-cyclodiphosphate (MECPP). Next, MSCPP is reductively converted to 1-hydroxy-2-methyl-2-(E)-butenyl 4-phosphate (HMBPP). Further, IPP and DMAPP are biosynthesized from HMBPP.

SUMMARY OF THE INVENTION

Now, it is an object of the present invention to isolate the gene cluster involved in the biosynthesis of IPP in the non-mevalonate pathway of *Hevea brasiliensis*, and to analyze the nucleotide sequence of each of the genes composing the gene cluster.

The sequences which are assumed to be the gene cluster involved in the biosynthesis of IPP in the non-mevalonate pathway are identified by syntactic analysis of the information on the gene fragment obtained through EST (Expression Sequence Tags) analysis of *Hevea brasiliensis* and known gene databases, and the gene homologs in relation to the non-mevalonate pathway are obtained by full-length cDNA cloning. Then the nucleotide sequences of each of the obtained genes are determined.

The gene cluster of the present invention involved in the biosynthesis of IPP by the non-mevalonate pathway is involved in the biosynthesis of vitamin E and carotenoids, so useful plants containing vitamin E and carotenoids at a high amount can be produced by transforming plants by the gene cluster obtained by the present invention. More specifically, the transformed *Hevea brasiliensis* obtained by introducing the genes of the present invention can be expected to produce a high-quality rubber with improved permanence. Especially, accompanied with the increased vitamin E content, many effects can be expected, including reduction of the quantity of synthetic antioxidants added when processing rubber.

BRIEF DESCRIPTION OF THE DRAWINGS

FIG. 2 is a photograph showing the result of complementation assay of 1-deoxy-D-xylulose-5-phosphate reductoisomerase.

FIG. 3 is a photograph showing the result of complementation assay of 2-C-methyl-D-erythritol-4-phosphate cytidyltransferase.

BEST MODE FOR CARRYING OUT THE INVENTION

Figure 1:
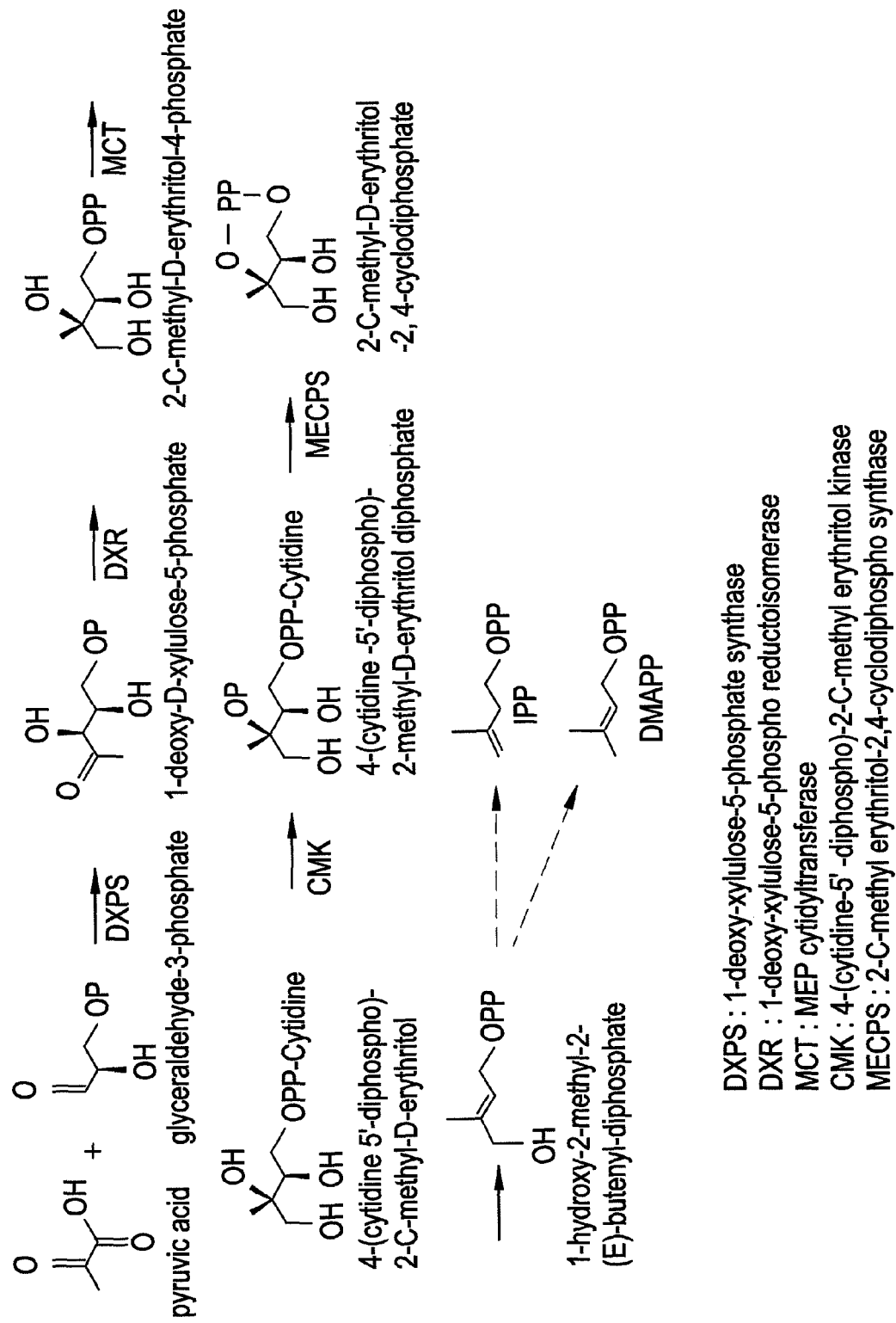
FIG. 1 is a figure showing the details of the mevalonate pathway.

In order to achieve the object above, the inventors of the present invention have determined gene nucleotide sequences by EST analysis and cDNA cloning. Total RNA was extracted from latex of the standard tree and xylem of the current year branch of *Hevea brasiliensis* so as to prepare cDNA libraries. Exhaustive one-pass sequence analysis was performed on these libraries. Then 16407 EST sequences were obtained from the cDNA library prepared from the latex and 16305 EST sequences from the cDNA library were obtained from the xylem with high accuracy (Total 32442). On the obtained partial sequences, clustering analysis based on similarity between sequences and annotation analysis based on comparison with known genes were performed, and thus an EST database of *Hevea brasiliensis* was constructed.

In the obtained EST database, the inventors have found EST sequences which are thought to encode enzymes of the non-mevalonate pathway, more specifically, 1-deoxy-D-xylulose-5-phosphate synthase, 1-deoxy-D-xylulose-5-phosphate reductoisomerase, 2-C-methyl-D-erythritol-4-phosphate cytidyltransferase, 4-(cytidine-5'-diphospho)-2-C-methyl-D-erythritol kinase, 2-C-methyl-D-erythritol 2,4-cyclodiphosphate synthase, 1-hydroxy-2-methyl-2-(E)-butenyl-4-diphosphate synthase, and 1-hydroxy-2-methyl-butenyl-4-diphosphate reductase. Moreover, as to these sequences, the inventors have determined the 3'terminal sequence by 3'-RACE (Rapid Amplification of cDNA Ends) and obtained full-length cDNAs.

A gene encoding 1-deoxy-D-xylulose-5-phosphate synthase is represented by nucleotide numbers from 1 to 2591 in SEQ ID NO:1 in the sequence list. The part corresponding to nucleotide numbers from 235 to 2394 in the nucleotide sequence in SEQ ID NO:1 in the sequence list corresponds to the open reading frame. A deduced amino acid sequence of 1-deoxy-D-xylulose-5-phosphate synthase obtained from the nucleotide sequence of the open reading frame is represented by amino acid numbers from 1 to 720 in SEQ ID NO:2 in the sequence list. Meanwhile, the 1-deoxy-D-xylulose-5-phosphate synthase is an enzyme that catalyzes the reaction which biosynthesizes 1-deoxy-D-xylulose-5-phosphate using pyruvic acid and glyceraldehyde-3-phosphate as substrate.

A gene encoding 1-deoxy-D-xylulose-5-phosphate reductoisomerase is represented by nucleotide numbers from 1 to 1929 in SEQ ID NO:3 in the sequence list. Meanwhile, this sequence contains the sequence of a vector, and the part excluded with the vector part corresponds to nucleotide numbers from 1 to 1884 in the nucleotide sequence in SEQ ID NO:3 in the sequence list. The part corresponding to nucleotide numbers from 301 to 1713 in the nucleotide sequence in SEQ ID NO:3 in the sequence list corresponds to an open reading frame. Meanwhile, this part contains the sequence of a vector, and the open reading frame excluded with the vector corresponds to nucleotide numbers from 256 to 1671 in the nucleotide sequence in SEQ ID NO:3 in the sequence list. A deduced amino acid sequence of 1-deoxy-D-xylulose-5-phosphate reductoisomerase obtained from the nucleotide sequence of the open reading frame is represented by amino acid numbers from 1 to 471 in SEQ ID NO:4 in the sequence list. Meanwhile, the 1-deoxy-D-xylulose-5-phosphate reductoisomerase is an enzyme that catalyzes the reaction which biosynthesizes 2-C-methyl-D-erythritol-4-phosphate using 1-deoxy-D-xylulose-5-phosphate as substrate.

A Gene encoding 2-C-methyl-D-erythritol-4-phosphate cytidyltransferase is represented by nucleotide numbers from 1 to 1335 in SEQ ID NO:5 in the sequence list. Meanwhile, this sequence contains the sequence of a vector, and the part excluded with the vector part corresponds to nucleotide numbers from 1 to 1301 in the nucleotide sequence in SEQ ID NO:5 in the sequence list. The part corresponding to nucleotide numbers from 214 to 1146 in the nucleotide sequence in SEQ ID NO:5 in the sequence list corresponds to an open reading frame. Meanwhile, this part contains the sequence of a vector, and the open reading frame excluded with the vector corresponds to nucleotide numbers from 180 to 1115 in the nucleotide sequence in SEQ ID NO:5 in the sequence list. A deduced amino acid sequence of 2-C-methyl-D-erythritol-4-phosphate cytidyltransferase obtained from the nucleotide sequence of the open reading frame is represented by amino acid numbers from 1 to 311 in SEQ ID NO:6 in the sequence list. Meanwhile, the 2-C-methyl-D-erythritol-4-phosphate cytidyltransferase is an enzyme that catalyzes the reaction which biosynthesizes 4-(cytidine-5'-diphospho)-2-C-methyl-D-erythritol using 2-C-methyl-D-erythritol-4-phosphate as substrate.

A Gene encoding 2-C-methyl-D-erythritol-4-phosphate cytidyltransferase obtained from another clone is represented by nucleotide numbers from 1 to 2069 in SEQ ID NO:7 in the sequence list. Meanwhile, this sequence contains the sequence of a vector, and the part excluded with the vector part corresponds to nucleotide numbers from 1 to 1254 in the nucleotide sequence in SEQ ID NO:7 in the sequence list. The part corresponding to nucleotide numbers from 185 to 1117 in the nucleotide sequence in SEQ ID NO:7 in the sequence list corresponds to an open reading frame. Meanwhile, this part contains the sequence of a vector, and the open reading frame excluded with the vector corresponds to nucleotide numbers from 150 to 1085 in the nucleotide sequence in SEQ ID NO:7 in the sequence list. A deduced amino acid sequence of 2-C-methyl-D-erythritol-4-phosphate cytidyltransferase obtained from the nucleotide sequence of the open-reading frame is represented by amino acid numbers from 1 to 311 in SEQ ID NO:8 in the sequence list. Meanwhile, the 2-C-methyl-D-erythritol-4-phosphate cytidyltransferase is an enzyme that catalyzes the reaction which biosynthesizes 4-(cytidine-5'-diphospho)-2-C-methyl-D-erythritol using 2-C-methyl-D-erythritol-4-phosphate as substrate.

A gene encoding 4-(cytidine-5'-diphospho)-2-C-methyl-D-erythritol kinase is represented by nucleotide numbers from 1 to 1512 in SEQ ID NO:9 in the sequence list. The part corresponding to nucleotide numbers from 110 to 1276 in the nucleotide sequence in SEQ ID NO:9 in the sequence list corresponds to the open reading frame. A deduced amino acid sequence of 4-(cytidine-5'-diphospho)-2-C-methyl-D-erythritol kinase obtained from the nucleotide sequence of the open reading frame is represented by amino acid numbers from 1 to 388 in SEQ ID NO:10 in the sequence list. Meanwhile, the 4-(cytidine-5'-diphospho)-2-C-methyl-D-erythritol kinase is an enzyme that catalyzes the reaction which biosynthesizes 4-(cytidine-5'-diphospho)-2-C-methyl-D-erythritol diphosphate using 4-(cytidine-5'-diphospho)-2-C-methyl-D-erythritol as substrate.

A gene encoding 2-C-methyl-D-erythritol 2,4-cyclodiphosphate synthase is represented by nucleotide numbers from 1 to 1036 in SEQ ID NO:11 in the sequence list. The part corresponding to nucleotide numbers from 1 to 714 in the nucleotide sequence in SEQ ID NO:11 in the sequence list corresponds to the open reading frame. A deduced amino acid sequence of 2-C-methyl-D-erythritol 2,4-cyclodiphosphate synthase obtained from the nucleotide sequence of the open reading frame is represented by amino acid numbers from 1 to 237 in SEQ ID NO:12 in the sequence list. Meanwhile, the 2-C-methyl-D-erythritol 2,4-cyclodiphosphate synthase is an enzyme that catalyzes the reaction which biosynthesizes 2-C-methyl-D-erythritol 2,4-cyclodiphosphate using 4-(cytidine-5'-diphospho)-2-C-methyl-D-erythrithol diphosphate as substrate.

A gene encoding 2-C-methyl-D-erythritol 2,4-cyclodiphosphate synthase obtained from another clone is represented by nucleotide numbers from 1 to 989 in SEQ ID NO:13 in the sequence list. The part corresponding to nucleotide numbers from 49 to 774 in the nucleotide sequence in SEQ ID NO:13 in the sequence list corresponds to the open reading frame. A deduced amino acid sequence of 2-C-methyl-D-erythritol 2,4-cyclodiphosphate synthase obtained from the nucleotide sequence of the open reading frame is represented by amino acid numbers from 1 to 241 in SEQ ID NO:14 in the sequence list. Meanwhile, the 2-C-methyl-D-erythritol 2,4-cyclodiphosphate synthase is an enzyme that catalyzes the reaction which biosynthesizes 2-C-methyl-D-erythritol 2,4-cyclodiphosphate using 4-(cytidine-5'-diphospho)-2-C-methyl-D-erythrithol diphosphate as substrate.

A gene encoding 1-hydroxy-2-methyl-2-(E)-butenyl-4-diphosphate synthase is represented by nucleotide numbers from 1 to 2745 in SEQ ID NO:15 in the sequence list. Meanwhile, this sequence contains the sequence of a vector, and the part excluded with the vector part corresponds to nucleotide numbers from 1 to 2713 in the nucleotide sequence in SEQ ID NO:15 in the sequence list. The part corresponding to nucleotide numbers from 184 to 2403 in the nucleotide sequence in SEQ ID NO:15 in the sequence list corresponds to an open reading frame. Meanwhile, this part contains the sequence of a vector, and the open reading frame excluded with the vector corresponds to nucleotide numbers from 152 to 2374 in the nucleotide sequence in SEQ ID NO:15 in the sequence list. A deduced amino acid sequence of 1-hydroxy-2-methyl-2-(E)-butenyl-4-diphosphate synthase obtained from the nucleotide sequence of the open reading frame is represented by amino acid numbers from 1 to 740 in SEQ ID NO:16 in the sequence list. Meanwhile, the 1-hydroxy-2-methyl-2-(E)-butenyl-4-diphosphate synthase is an enzyme that catalyzes the reaction which biosynthesizes 1-hydroxy-2-methyl-2-(E)-butenyl-4-diphosphate using 2-C-methyl-D-erythritol-2,4-cyclo diphosphate as substrate.

A gene encoding 1-hydroxy-2-methyl-butenyl-4-diphosphate reductase is represented by nucleotide numbers from 1 to 1682 in SEQ ID NO:17 in the sequence list. Meanwhile, this sequence contains the sequence of a vector, and the part excluded with the vector part corresponds to nucleotide numbers from 1 to 1632 in the nucleotide sequence in SEQ ID NO:17 in the sequence list. The part corresponding to nucleotide numbers from 107 to 1492 in the nucleotide sequence in SEQ ID NO:17 in the sequence list corresponds to an open reading frame. Meanwhile, this part contains the sequence of a vector, and the open reading frame excluded with the vector corresponds to nucleotide numbers from 57 to 1445 in the nucleotide sequence in SEQ ID NO:17 in the sequence list. A deduced amino acid sequence of 1-hydroxy-2-methyl-butenyl-4-diphosphate reductase obtained from the nucleotide sequence of the Open reading frame is represented by amino acid numbers from 1 to 462 in SEQ ID NO:18 in the sequence list. Meanwhile, the 1-hydroxy-2-methyl-butenyl-4-diphosphate reductase is an enzyme that catalyzes the reaction which biosynthesizes isopentenyl diphosphate and dimethylallyl diphosphate using 1-hydroxy-2-methyl-2-(E)-butenyl-4-diphosphate as substrate.

According to recombinant DNA techniques, artificial mutation can be made to a particular site of the original DNA, without changing the fundamental properties of the DNA or in such a way as to improve these properties. As to genes having natural nucleotide sequences provided according to the present invention or even genes having nucleotide sequences different from the natural sequence, artificial insertion, deletion and substitution can be performed in the same manner, and they can be altered to have an equal or improved properties as the natural genes. Moreover, the present invention includes such mutated genes.

More specifically, a gene consisting of a nucleotide sequence in which a part of the nucleotide sequence shown in SEQ ID NO:1 in the sequence list has been deleted, substituted or added means a gene in which no more than 20, preferably no more than 10, more preferably no more than 5 nucleotide sequences in the nucleotide sequence in SEQ ID NO:1 have been substituted. Furthermore, such a gene has no less than 95%, preferably no less than 97%, more preferably no less than 99% homology with the nucleotide sequence shown in SEQ ID NO:1. Even such a gene is also within the scope of the present invention, as long as the gene encodes a protein having the function as 1-deoxy-D-xylulose-5-phosphate synthase, which biosynthesizes 1-deoxy-D-xylulose-5-phosphate using pyruvic acid and glyceraldehyde-3-phosphate as substrate. Additionally, such a gene hybridizes with the gene shown in SEQ ID NO:1 under stringent conditions.

Similarly, a gene consisting of a nucleotide sequence in which a part of the nucleotide sequence shown in SEQ ID NO:3 in the sequence list has been deleted, substituted or added means a gene in which no more than 20, preferably no more than 10, more preferably no more than 5 nucleotide sequences in the nucleotide sequence in SEQ ID NO:3 have been substituted. Furthermore, such a gene has no less than 95%, preferably no less than 97%, more preferably no less than 99% homology with the nucleotide sequence shown in SEQ ID NO:3. Even such a gene is also within the scope of the present invention, as long as the gene encodes a protein having the function as 1-deoxy-D-xylulose-5-phosphate reductoisomerase, which biosynthesizes 2-C-methyl-D-erythritol-4-phosphate using 1-deoxy-D-xylulose-5-phosphate as substrate. Additionally, such a gene hybridizes with the gene shown in SEQ ID NO:3 under stringent conditions.

Similarly, a gene consisting of a nucleotide sequence in which a part of the nucleotide sequence shown in SEQ ID NO:5 in the sequence list has been deleted, substituted or added means a gene in which no more than 20, preferably no more than 10, more preferably no more than 5 nucleotide sequences in the nucleotide sequence in SEQ ID NO:5 have been substituted. Furthermore, such a gene has no less than 95%, preferably no less than 97%, more preferably no less than 99% homology with the nucleotide sequence shown in SEQ ID NO:5. Even such a gene is also within the scope of the present invention, as long as the gene encodes a protein having the function as 2-C-methyl-D-erythritol-4-phosphate cytidyltransferase, which biosynthesizes 4-(cytidine-5'-diphospho)-2-C-methyl-D-erythritol using 2-C-methyl-D-erythritol-4-phosphate as substrate. Additionally, such a gene hybridizes with the gene shown in SEQ ID NO:5 under stringent conditions.

Similarly, a gene consisting of a nucleotide sequence in which a part of the nucleotide sequence shown in SEQ ID NO:7 in the sequence list has been deleted, substituted or added means a gene in which no more than 20, preferably no more than 10, more preferably no more than 5 nucleotide sequences in the nucleotide sequence in SEQ ID NO:7 have been substituted. Further, such a gene has no less than 95%, preferably no less than 97%, more preferably no less than 99% homology with the nucleotide sequence shown in SEQ ID NO:7. Even such a gene is also within the scope of the present invention, as long as the gene encodes a protein having the function as 2-C-methyl-D-erythritol-4-phosphate cytidyltransferase, which biosynthesizes 4-(cytidine-5'-diphospho)-2-C-methyl-D-erythritol using 2-C-methyl-D-erythritol-4-phosphate as substrate. Additionally, such a gene hybridizes with the gene shown in SEQ ID NO:7 under stringent conditions.

Similarly, a gene consisting of a nucleotide sequence in which a part of the nucleotide sequence shown in SEQ ID NO:9 in the sequence list has been deleted, substituted or added means a gene in which no more than 20, preferably no more than 10, more preferably no more than 5 nucleotide sequences in the nucleotide sequence in SEQ ID NO:9 have been substituted. Further, such a gene has no less than 95%, preferably no less than 97%, more preferably no less than 99% homology with the nucleotide sequence shown in SEQ ID NO:9. Even such a gene is also within the scope of the present invention, as long as the gene encodes a protein having the function as 4-(cytidine-5'-diphospho)-2-C-methyl-D-erythritol kinase, which biosynthesizes 4-(cytidine-5'-diphospho)-2-C-methyl-D-erythritol diphosphate using 4-(cytidine-5'-diphospho)-2-C-methyl-D-erythritol as substrate. Additionally, such a gene hybridizes with the gene shown in SEQ ID NO:9 under stringent conditions.

Similarly, a gene consisting of a nucleotide sequence in which a part of the nucleotide sequence shown in SEQ ID NO:11 in the sequence list has been deleted, substituted or added means a gene in which no more than 20, preferably no more than 10, more preferably no more than 5 nucleotide sequences in the nucleotide sequence in SEQ ID NO:11 have been substituted. Further, such a gene has no less than 95%, preferably no less than 97%, more preferably no less than 99% homology with the nucleotide sequence shown in SEQ ID NO:11. Even such a gene is also within the scope of the present invention, as long as the gene encodes a protein having the function as 2-C-methyl-D-erythritol 2,4-cyclodiphosphate synthase, which biosynthesizes 2-C-methyl-D-erythritol 2,4-cyclodiphosphate using 4-(cytidine-5'-diphospho)-2-C-methyl-D-erythrithol diphosphate as substrate. Additionally, such a gene hybridizes with the gene shown in SEQ ID NO:11 under stringent conditions.

Similarly, a gene consisting of a nucleotide sequence in which a part of the nucleotide sequence shown in SEQ ID NO:13 in the sequence list has been deleted, substituted or added means a gene in which no more than 20, preferably no more than 10, more preferably no more than 5 nucleotide sequences in the nucleotide sequence in SEQ ID NO:13 have been substituted. Further, such a gene has no less than 95%, preferably no less than 97%, more preferably no less than 99% homology with the nucleotide sequence shown in SEQ ID NO:13. Even such a gene is also within the scope of the present invention, as long as the gene encodes a protein having the function as 2-C-methyl-D-erythritol 2,4-cyclodiphosphate synthase, which biosynthesizes 2-C-methyl-D-erythritol 2,4-cyclodiphosphate using 4-(cytidine-5'-diphospho)-2-C-methyl-D-erythrithol diphosphate as substrate. Additionally, such a gene hybridizes with the gene shown in SEQ ID NO:13 under stringent conditions.

Similarly, a gene consisting of a nucleotide sequence in which a part of the nucleotide sequence shown in SEQ ID NO:15 in the sequence list has been deleted, substituted or added means a gene in which no more than 20, preferably no more than 10, more preferably no more than 5 nucleotide sequences in the nucleotide sequence in SEQ ID NO:15 are substituted. Further, such a gene has no less than 95%, preferably no less than 97%, more preferably no less than 99% homology with the nucleotide sequence shown in SEQ ID NO:15. Even such a gene is also within the scope of the present invention, as long as the gene encodes a protein having the function as 1-hydroxy-2-methyl-2-(E)-butenyl-4-diphosphate synthase which biosynthesizes 1-hydroxy-2-methyl-2-(E)-butenyl-4-diphosphate using 2-C-methyl-D-erythritol-2,4-cyclo diphosphate as substrate. Additionally, such a gene hybridizes with the gene shown in SEQ ID NO:15 under stringent conditions.

Similarly, a gene consisting of a nucleotide sequence in which a part of the nucleotide sequence shown in SEQ ID NO:17 in the sequence list has been deleted, substituted or added means a gene in which no more than 20, preferably no more than 10, more preferably no more than 5 nucleotide sequences in the nucleotide sequence in SEQ ID NO:17 have been substituted. Further, such a gene has no less than 95%, preferably no less than 97%, more preferably no less than 99% homology with the nucleotide sequence shown in SEQ ID NO:17. Even such a gene is also within the scope of the present invention, as long as the gene encodes a protein having the function as 1-hydroxy-2-methyl-butenyl-4-diphosphate reductase which biosynthesizes isopentenyl diphosphate and dimethylallyl diphosphate using 1-hydroxy-2-methyl-2-(E)-butenyl-4-diphosphate as substrate. Additionally, such a gene hybridizes with the gene shown in SEQ ID NO:17 under stringent conditions.

Those skilled in the art may select conditions for hybridization ad libitum. A membrane onto which a DNA or RNA molecule to be tested has been transferred and a labeled probe can be hybridized in an applicable hybridization buffer. The hybridization buffer may be composed of 5×SSC, 0.1 weight % N-lauroyl sarcosine, 0.02 weight % SDS, 2 weight % blocking reagent for nucleotide sequence hybridization, and 50 weight % formamide, for instance. As the blocking reagent for nucleotide sequence hybridization, for example, commercially available blocking reagent for nucleotide sequence hybridization can be dissolved into a buffer solution (pH 7.5) composed of 0.1 M maleic acid and 0.15 M NaCl to make the concentration of the blocking reagent to be 10%. 20×SSC may be composed of 3M NaCl and 0.3 M citric acid solution. SSC may be used preferably at 3 to 6×SSC concentration, and more preferably at 4 to 5×SSC concentration.

Hybridization may be performed at 40 to 80° C., preferably at 50 to 70° C., and more preferably at 55 to 65° C. Washing may be performed using a washing buffer after incubation for several hours or overnight. Washing may be performed preferably at room temperature, and more preferably at the temperature of hybridization. The washing buffer may be composed of 6×SSC+0.1 weight % SDS solution, preferably composed of 4×SSC+0.1 weight % SDS solution, more preferably composed of 2×SSC+0.1 weight % SDS solution, even more preferably composed of 1×SSC+0.1 weight % SDS solution, and most preferably composed of 0.1×SSC+0.1 weight % SDS solution. The membrane can be washed with such a washing buffer and the DNA molecule or RNA molecule hybridized with the probe can be identified by the label used for the probe.

Further herein, a protein consisting of an amino acid sequence in which a part of the amino acid sequence shown in SEQ ID NO:2 has been deleted, substituted or added means a protein in which no more than 20, preferably no more than 10, more preferably no more than 5 amino acids in the amino acid sequence in SEQ ID NO:2 have been substituted. Further, such a protein has no less than 95%, preferably no less than 97%, more preferably no less than 99% homology with the amino acid sequence shown in SEQ ID NO:2. Even such a protein is within the scope of the present invention, as long as the protein has the function as 1-deoxy-D-xylulose-5-phosphate synthase, which biosynthesizes 1-deoxy-D-xylulose-5-phosphate using pyruvic acid and glyceraldehyde-3-phosphate as substrate.

Further herein, a protein consisting of an amino acid sequence in which a part of the amino acid sequence shown in SEQ ID NO:4 has been deleted, substituted or added means a protein in which no more than 20, preferably no more than 10, more preferably no more than 5 amino acids in the amino acid sequence in SEQ ID NO:4 have been substituted. Further, such a protein has no less than 95%, preferably no less than 97%, more preferably no less than 99% homology with the amino acid sequence shown in SEQ ID NO:4. Even such a protein is within the scope of the present invention, as long as the protein has the function as 1-deoxy-D-xylulose-5-phosphate reductoisomerase which biosynthesizes 2-C-methyl-D-erythritol-4-phosphate using 1-deoxy-D-xylulose-5-phosphate as substrate.

Similarly, a protein consisting of an amino acid sequence in which a part of the amino acid sequence shown in SEQ ID NO:6 in the sequence list has been deleted, substituted or added means a protein in which no more than 20, preferably no more than 10, more preferably no more than 5 amino acids in the amino acid sequence in SEQ ID NO:6 have been substituted. Further, such a protein has no less than 95%, preferably no less than 97%, more preferably no less than 99% homology with the amino acid sequence shown in SEQ ID NO:6. Even such a protein is within the scope of the present invention, as long as the protein has the function as 2-C-methyl-D-erythritol-4-phosphate cytidyltransferase which biosynthesizes 4-(cytidine-5'-diphospho)-2-C-methyl-D-erythritol using 2-C-methyl-D-erythritol-4-phosphate as substrate.

Similarly, a protein consisting of an amino acid sequence in which a part of the amino acid sequence shown in SEQ ID NO:8 in the sequence list has been deleted, substituted or added means a protein in which no more than 20, preferably no more than 10, more preferably no more than 5 amino acids in the amino acid sequence in SEQ ID NO:8 have been substituted. Further, such a protein has no less than 95%, preferably no less than 97%, more preferably no less than 99% homology with the amino acid sequence shown in SEQ ID NO:8. Even such a protein is within the scope of the present invention, as long as the protein has the function as 2-C-methyl-D-erythritol-4-phosphate cytidyltransferase which biosynthesizes 4-(cytidine-5'-diphospho)-2-C-methyl-D-erythritol using 2-C-methyl-D-erythritol-4-phosphate as substrate.

Similarly, a protein consisting of an amino acid sequence in which a part of the amino acid sequence shown in SEQ ID NO:10 in the sequence list has been deleted, substituted or added means a protein in which no more than 20, preferably no more than 10, more preferably no more than 5 amino acids in the amino acid sequence in SEQ ID NO:10 have been substituted. Further, such a protein has no less than 95%, preferably no less than 97%, more preferably no less than 99% homology with the amino acid sequence shown in SEQ ID NO:10. Even such a protein is within the scope of the present invention, as long as the protein has the function as 4-(cytidine-5'-diphospho)-2-C-methyl-D-erythritol kinase which biosynthesizes 4-(cytidine-5'-diphospho)-2-C-methyl-D-erythritol diphosphate using 4-(cytidine-5'-diphospho)-2-C-methyl-D-erythritol as substrate.

Similarly, a protein consisting of an amino acid sequence in which a part of the amino acid sequence shown in SEQ ID NO:12 in the sequence list has been deleted, substituted or added means a protein in which no more than 20, preferably no more than 10, more preferably no more than 5 amino acids in the amino acid sequence in SEQ ID NO:12 have been substituted. Further, such a protein has no less than 95%, preferably no less than 97%, more preferably no less than 99% homology with the amino acid sequence shown in SEQ ID NO:12. Even such a protein is within the scope of the present invention, as long as the protein has the function as 2-C-methyl-D-erythritol 2,4-cyclodiphosphate synthase which biosynthesizes 2-C-methyl-D-erythritol 2,4-cyclodiphosphate using 4-(cytidine-5'-diphospho)-2-C-methyl-D-erythrithol diphosphate as substrate.

Similarly, a protein consisting of an amino acid sequence in which a part of the amino acid sequence shown in SEQ ID NO:14 in the sequence list has been deleted, substituted or added means a protein in which no more than 20, preferably no more than 10, more preferably no more than 5 amino acids in the amino acid sequence in SEQ ID NO:14 have been substituted. Further, such a protein has no less than 95%, preferably no less than 97%, more preferably no less than 99% homology with the amino acid sequence shown in SEQ ID NO:14. Even such a protein is within the scope of the present invention, as long as the protein has the function as 2-C-methyl-D-erythritol 2,4-cyclodiphosphate synthase which biosynthesizes 2-C-methyl-D-erythritol 2,4-cyclodiphosphate using 4-(cytidine-5'-diphospho)-2-C-methyl-D-erythrithol diphosphate as substrate.

Similarly, a protein consisting of an amino acid sequence in which a part of the amino acid sequence shown in SEQ ID NO:16 in the sequence list has been deleted, substituted or added means a protein in which no more than 20, preferably no more than 10, more preferably no more than 5 amino acids in the amino acid sequence in SEQ ID NO:16 have been substituted. Further, such a protein has have no less than 95%, preferably no less than 97%, more preferably no less than 99% homology with the amino acid sequence shown in SEQ ID NO:16. Even such a protein is within the scope of the present invention, as long as the protein has the function as 1-hydroxy-2-methyl-2-(E)-butenyl-4-diphosphate synthase which biosynthesizes 1-hydroxy-2-methyl-2-(E)-butenyl-4-diphosphate using 2-C-methyl-D-erythritol-2,4-cyclo diphosphate as substrate.

Similarly, a protein consisting of an amino acid sequence in which a part of the amino acid sequence shown in SEQ ID NO:18 in the sequence list has been deleted, substituted or added means a protein in which no more than 20, preferably no more than 10, more preferably no more than 5 amino acids in the amino acid sequence in SEQ ID NO:18 have been substituted. Further, such a protein has no less than 95%, preferably no less than 97%, more preferably no less than 99% homology with the amino acid sequence shown in SEQ ID NO:18. Even such a protein is within the scope of the present invention, as long as the protein has the function as 1-hydroxy-2-methyl-butenyl-4-diphosphate reductase which biosynthesizes isopentenyl diphosphate and dimethylallyl diphosphate using 1-hydroxy-2-methyl-2-(E)-butenyl-4-diphosphate as substrate.

The gene cluster of the present invention involved in the biosynthesis of isopentenyl diphosphate in the non-mevalonate pathway can be introduced into plants such as rubber tree to enhance its expression, so that gene products from the non-mevalonate pathway can be increased in said plants. Not polyisoprene (rubber component), which is the major component of latex, but many non-rubber components can be synthesized in the non-mevalonate pathway. Especially, tocotrienol and carotenoid, which are vitamin Es, are known to exert antioxidant effects in natural rubber made from processed latex, so if this component is increased, improvement in permanence of rubber material can be expected. Further herein, "to improve the property of the rubber" means to have desired effects of improving permanence on the rubber material obtained by increasing Vitamin E or carotenoid content in natural rubber.

The plant to be introduced with gene of the present invention is not limited to *Hevea brasiliensis*, the examples of other plants may be guayule, cassava, sunflower, lettuce, Indian rubber tree, and etc., but the target plants to be transformed are not limited to these plants, and transformants into which the gene of the present invention has been introduced can be produced in various plants. Particularly, according to this invention, it is preferable to transform rubber-producing plants, such as *Hevea Brasiliensis*, in order to improve the quality of the rubber obtained from said rubber-producing plants. Rubber-producing plants are known to spread wide variety of families including Asteraceae, Moraceae, Euphorbiaceae, Asclepiadaceae, and Apocynaceae.

As a method for producing transformants, usual methods known in the art can be used. As an useful promoter for activating the introduced gene, the cauliflower mosaic virus 35S promoter widely used in the art, for example, can be used and positioned upstream of the gene of the present invention, which is to be transduced. In many cases, some promoter is required to achieve sufficient expression of the introduced foreign gene. The preferred promoter is not limited to the cauliflower mosaic virus 35S promoter, and various promoters widely used in the art may also be used.

Furthermore, the vectors which can be used in the present invention may include, but not limited to, vectors such as pIG121-Hm, pBI12, pBI221, pBIN19, pCC22, pGA482, pPCV001, pCGN1547, pJJ1881, pPZP111, pGreen0029, pBI101, pBI121, and pYLTAC7. Transgenic plants can be prepared by introducing such vectors into *Agrobacterium*, for instance, to have a callus or a plantlet infected, and thus seeds derived from such transgenic plants can be obtained. Further, the transformation method for introducing the plant gene of the present invention into plants is not limited to the *Agrobacterium* method, but various methods commonly used in the art including the particle gun method and the electroporation method may also be used. Additionally, an example in which a foreign gene is introduced into rubber tree for transformation is disclosed in Japanese Patent Publication No. 1996-116977. Therefore, those skilled in the art can produce a transgenic plant, into which the gene of the present invention has been introduced, by making appropriate alterations with reference to the description of Japanese Patent Publication No. 1996-116977.

EXAMPLES

The present invention will be specifically described below with reference to examples, but the scope of the present inventions will not be limited to these examples.

(Materials)

Latex and xylem from the current year branch of *Hevea brasiliensis* standard tree PRIM 600 cultivated in Cikampek, Indonesia were used as a plant sample. The latex was suspended in an equal amount of 2× sampling buffer (0.1 M Tris-HCL, 0.3 M LiCl, 0.01 M EDTA, 10% SDS) immediately after sampling the latex. Also, a mutant *E. coli* strain used was gifted from associate professor Tomohisa Kuzuyama, Biotechnology Research Center of the University of Tokyo.

(RNA Extraction from *Hevea brasiliensis*)

RNA was extracted from the latex and xylem respectively by the following procedures. Immediately after sampling, the sample (equivalent to 25 ml of latex) suspended in an equal amount of 2× sampling buffer (0.1 M Tris-HCL, 0.3 M LiCl, 0.01 M EDTA, 10% SDS) was centrifuged, and the upper layer constituting the rubber layer was removed. Then, 1.5 equivalent amount of 2× CTAB solution (2% Hexadecyltrimethylammonium bromide(CTAB), 1% 2-mercaptoethanol, 0.1 M Tris-HCL (pH9.5), 1.4 M NaCl, 20 mM EDTA) was added. After incubating at 65° C. for 10 minutes, treatment with chloroform/isoamyl alcohol was performed (repeated twice). A ¼ amount of 10 M LiCl was added to the collected aqueous layer and mixed, then incubated at −20° C. for 2 hours (selective precipitation of RNA). It was centrifuged, the precipitation was dissolved into an appropriate amount of TE, then centrifuged, and the supernatant was collected (polysaccharides were removed). Further, the fraction was treated with phenol, phenol/chloroform, chloroform/isoamyl alcohol, and then selective precipitation of RNA by LiCl was performed again. The precipitation was cleaned with 70% ethanol, and dissolved in DEPC-treated water after being dried under reduced pressure. Thus, total RNA derived from latex was obtained.

Also, the phloem of the current year branch was peeled off by a knife to obtain about 1 g of xylem, and it was pound in a mortar with a pestle while cooling with liquid nitrogen. The total RNA derived from xylem was obtained using RNeasy Plant Mini Kit (registered trademark, Qiagen).

The obtained RNA solution was quantified by optical density measurements, and this was confirmed by electrophoresis. A 450 μg of RNA was obtained from 25 mg of latex, and 110 μg of RNA was obtained from 1 g of xylem.

(Preparation of cDNA Libraries of *Hevea brasiliensis*)

The cDNA libraries were prepared from the RNA samples derived from *Hevea brasiliensis* latex and xylem by the G-Capping method at Hitachi Instruments Service Co., Ltd. The G-Capping method is a method that can achieve full-length cDNAs at a high percentage.

The cDNA library derived from the latex has the library size of $1.7 \times 10^5$, the insert percentage of 71% (24 samples/agarose gel electrophoresis), and the percentage of full-length cDNA was 82% (toward clones with insert). The size of cDNA library derived from the xylem was $2.9 \times 10^5$, and the percentage of insert was 80% (24 samples/agarose gel electrophoresis), and the percentage of full-length cDNA was 87% (toward clones with insert).

(Sequence Analysis, Clustering Analysis and Annotation Analysis of EST Sequences)

At the Genome Information Science Laboratory of Kitasato Institute for Life Sciences of Kitasato University, exhaustive one-pass sequence analysis was performed on approximately 20,000 clones of the cDNA libraries derived from latex and xylem of *Hevea brasiliensis* respectively. According to the sequence information obtained from the sequence analysis, clones with no insert and clones failed to determine sequence were removed, then high accuracy sequence information was obtained. The latex cDNA library and xylem cDNA library provided 16407 EST sequences and 16305 EST sequences respectively with high accuracy (total 32442).

The obtained partial sequences were subjected to clustering analysis based on similarity between sequences, and annotation analysis based on comparison with known genes, thereby an EST database of *Hevea brasiliensis* was constructed. A VISUALBIO clustering of NTT Software was used for the clustering analysis. The annotation analysis was performed by homology search using NCBI BLAST. The database used for the search was nr (All non-redundant GenBank CDS translations+PDB+SwissProt+PIR (Peptide Sequence Database)).

In the obtained EST database, EST sequences of the enzymes involved in the non-mevalonate pathway were found, i.e. 1-deoxy-D-xylulose-5-phosphate synthase, 1-deoxy-D-xylulose-5-phosphate reductoisomerase, 2-C-methyl-D-erythritol-4-phosphate cytidylyltransferase, 4-(cytidine-5'-diphospho)-2-C-methyl-D-erythritol kinase, 2-C-methyl-D-erythritol 2,4-cyclodiphosphate synthase, 1-hydroxy-2-methyl-2-(E)-butenyl-4-diphosphate synthase, and 1-hydroxy-2-methyl-butenyl-4-diphosphate reductase.

(Determination of Sequences at the 3' Terminal by 3'-RACE)

The sequences at the 3' terminal were determined by 3'-RACE (Rapid Amplification of cDNA Ends) on each sequences obtained by the analyses above to obtain full-length cDNAs. For 3'-RACE, a 3'-Full RACE Core Set (Takara Bio Inc.) was used. An oligo-dT primer was used for reverse transcription. For amplification by PCR, an oligo-dT primer and a sense primer having sequence identity with a part of known sequences were used. The amplified fragments were obtained from reverse transcription and PCR, then the fragments were subjected to TA cloning into pT7Blue vector, which was succeeded by sequence analysis.

The sequences obtained in this way are as follows; (1) the nucleotide sequence of 1-deoxy-D-xylulose-5-phosphate synthase gene (SEQ ID NO:1 in the sequence list), (2) the nucleotide sequence of 1-deoxy-D-xylulose-5-phosphate reductoisomerase gene (SEQ ID NO:3 in the sequence list), (3) the nucleotide sequence of 2-C-methyl-D-erythritol-4-phosphate cytidyltransferase gene (SEQ ID NO:5 in the sequence list), (4) the nucleotide sequence of 2-C-methyl-D-erythritol-4-phosphate cytidyltransferase gene derived from another clone (SEQ ID NO:7 in the sequence list), (5) the nucleotide sequence of 4-(cytidine-5'-diphospho)-2-C-methyl-D-erythritol kinase gene (SEQ ID NO:9 in the sequence list), (6) the nucleotide sequence of 2-C-methyl-D-erythritol 2,4-cyclodiphosphate synthase gene (SEQ ID NO:11 in the sequence list), (7) the nucleotide sequence of 2-C-methyl-D-erythritol 2,4-cyclodiphosphate synthase gene derived from another clone (SEQ ID NO:13 in the sequence list), (8) the nucleotide sequence of 1-hydroxy-2-methyl-2-(E)-butenyl-4-diphosphate synthase gene (SEQ ID NO:15 in the sequence list), and (9) the nucleotide sequence of 1-hydroxy-2-methyl-butenyl-4-diphosphate reductase gene (SEQ ID NO:17 in the sequence list).

Additionally, the deduced amino acid sequences of the proteins obtained from the open reading frames of these nucleotide sequences are as follows; (1) the amino acid sequence of 1-deoxy-D-xylulose-5-phosphate synthase (SEQ ID NO:2 in the sequence list), (2) the amino acid sequence of 1-deoxy-D-xylulose-5-phosphate reductoisomerase (SEQ ID NO:4 in the sequence list), (3) the amino acid sequence of 2-C-methyl-D-erythritol-4-phosphate cytidyltransferase (SEQ ID NO:6 in the sequence list), (4) the amino acid sequence of 2-C-methyl-D-erythritol-4-phosphate cytidyltransferase derived from another clone (SEQ ID NO:8 in the sequence list), (5) the amino acid sequence of 4-(cytidine-5'-diphospho)-2-C-methyl-D-erythritol kinase (SEQ ID NO:10 in the sequence list), (6) the amino acid sequence of 2-C-methyl-D-erythritol 2,4-cyclodiphosphate synthase (SEQ ID NO:12 in the sequence list), (7) the amino acid sequence of 2-C-methyl-D-erythritol 2,4-cyclodiphosphate synthase derived from another clone (SEQ ID NO:14 in the sequence list), (8) the amino acid sequence of 1-hydroxy-2-methyl-2-(E)-butenyl-4-diphosphate synthase (SEQ ID NO:16 in the sequence list), and (9) the amino acid sequence of 1-hydroxy-2-methyl-butenyl-4-diphosphate reductase (SEQ ID NO:18 in the sequence list).

(Complementary Assay Using Transformed *E. coli*)

Among sequences obtained by the procedure as described above, the functions of the genes encoding 1-deoxy-D-xylulose-5-phosphate reductoisomerase, 2-C-methyl-D-erythritol-4-phosphate cytidyltransferase and 2-C-methyl-D-erythritol 2,4-cyclodiphosphate synthase were confirmed by complementary assay using transformed *E. coli* strains deficient of the above-mentioned corresponding genes.

PCR was performed using sense primers and antisense primers attached with appropriate restriction sites, the sequences corresponding to the reading frames of 1-deoxy-D-xylulose-5-phosphate reductoisomerase, 2-C-methyl-D-erythritol-4-phosphate cytidyltransferase and 2-C-methyl-D-erythritol 2,4-cyclodiphosphate synthase were amplified respectively. The amplified fragments were in frame cloned into pMW118 vector (Nippon gene).

The genes subjected to the analysis are indispensable for growth of *E. coli* strain. The strain deficient of 1-deoxy-D-xylulose-5-phosphate reductoisomerase gene, which was used as the background of the complementary assay, can grow on culture medium by adding 2-C-methylerythritol into the culture medium. Moreover, the strains deficient of 2-C-methyl-D-erythritol-4-phosphate cytidyltransferase and the strain deficient of 2-C-methyl-D-erythritol 2,4-cyclodiphosphate synthase are introduced with a plasmid (pTMV20KM) containing the gene cluster involved in mevalonate pathway derived from Streptomyces sp. CL190 strain. Therefore, the strains can grow by adding mevalonic acid into the medium owing to the enzymes involved in the mevalonic acid introduced into the strains. These *E. coli* mutant strains were gifted from associate professor Tomohisa Kuzuyama, Biotechnology Research Center of the University of Tokyo. Meanwhile, the strain deficient of 1-deoxy-D-xylulose-5-phosphate reductoisomerase used in this study is described in Kuzuyama et al., Biosci. Biotechnol. Biochem., 63(4), 776-778.1999, and the strains deficient of 2-C-methyl-D-erythritol-4-phosphate cytidyltransferase and the strain deficient of 2-C-methyl-D-erythritol 2,4-cyclodiphosphate synthase are described in Takagi et al., Tetrahedron Letters 41(2000)3395-3398, respectively.

The pMW118 vector was introduced into mutant strains, and the vector contained the reading frame region of the target gene derived from *Hevea Brasiliensis*. If the function of the transformed *E. coli* strain is complemented by the introduced target gene from *Hevea Brasiliensis*, it is assumed that the transformed *E. coli* may recover the ability to grow on the normal LB medium not containing 2-C-methylerythritol or mevalonic acid. By performing the complementation assay to identify the functions of the target genes, the functions of 1-deoxy-D-xylulose-5-phosphate reductoisomerase (one clone), 2-C-methyl-D-erythritol-4-phosphate cytidyltransferase (two clones) and 2-C-methyl-D-erythritol 2,4-cyclodiphosphate synthase (two clones) were confirmed. The concrete data will be described below.

Figure 4:
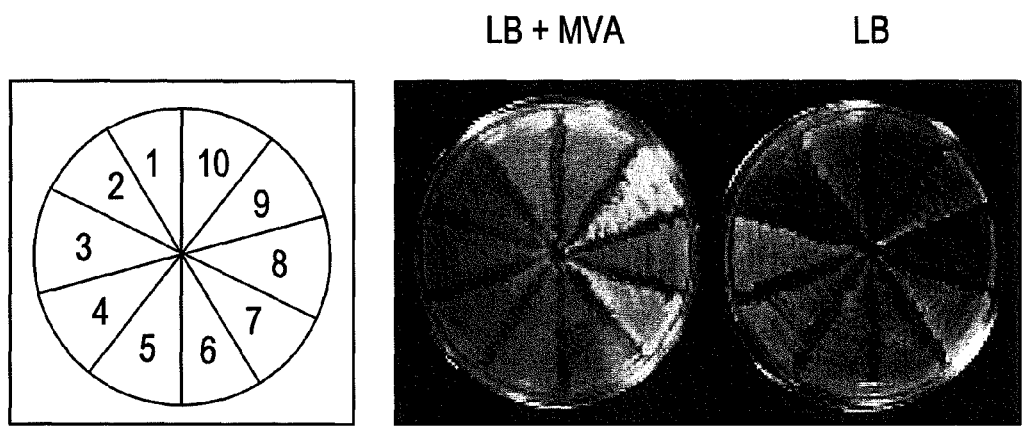
FIG. 4 is a photograph showing the result of complementation assay of 2-C-methyl-D-erythritol 2,4-cyclodiphosphate synthase.

The data on the complementary assay of 1-deoxy-D-xylulose-5-phosphate reductoisomerase is shown in FIG. 2, that of 2-C-methyl-D-erythritol-4-phosphate cytidyltransferase is shown in FIG. 3, and that of 2-C-methyl-D-erythritol 2,4-cyclodiphosphate synthase is shown in FIG. 4, respectively.

As well, in FIG. 2, the data corresponding to the portion 1 of the petri dish shows the series of the wild-type strain, the data corresponding to the portion 2 of the petri dish shows the series of the transformed *E. coli* strain, the data corresponding to the portion 3 of the petri dish shows the series of the transformed *E. coli* strain added with a genomic fragment of *E. coli* gene, the data corresponding to the portion 4 of the petri dish shows the series of the transformed *E. coli* strain added with an open reading frame from *E. coli* gene, the data corresponding to the portion 5 of the petri dish shows the series of the transformed *E. coli* strain added with an open reading frame from *Arabidopsis* gene, the data corresponding to the portion 6 of the petri dish shows the series of the transformed *E. coli* strain added with an open reading frame from *Arabidopsis* gene deleted with the signal sequence, the data corresponding to the portion 7 of the petri dish shows the series of the transformed *E. coli* strain added with an open reading frame from *Hevea brasiliensis* gene, and the data corresponding to the portion 8 of the petri dish shows the series of the transformed *E. coli* strain added with the open reading frame of *Arabidopsis* gene deleted with the signal sequence, respectively.

Moreover, in FIGS. 3 and 4, the data corresponding to the portion 1 of the petri dish shows the series of the wild-type strain, the data corresponding to the portion 2 of the petri dish shows the series of the transformed *E. coli* strain, the data corresponding to the portion 3 of the petri dish shows the series of the transformed *E. coli* strain added with a genomic fragment of *E. coli* gene, the data corresponding to the portion 4 of the petri dish shows the series of the transformed *E. coli* strain added with an open reading frame from *E. coli* gene, the data corresponding to the portion 5 of the petri dish shows the series of the transformed *E. coli* strain added with an open reading frame from *Arabidopsis* gene, the data corresponding to the portion 6 of the petri dish shows the series of the transformed *E. coli* strain added with an open reading frame from *Arabidopsis* gene deleted with the signal sequence, the data corresponding to the portions 7 and 9 of the petri dish show the series of the transformed *E. coli* strain added with an open reading frame from *Hevea brasiliensis* gene, and the data corresponding to the portions 8 and 10 of the petri dish show the series of the transformed *E. coli* strain added with an open reading frame of *Arabidopsis* gene deleted with the signal sequence, respectively.

As shown from FIG. 2 to FIG. 4, the wild-type strain grew normally as shown in portion 1 of the petri dish, while the *E. coli* mutant strain could not grow normally in this medium as shown in portion 2 of the petri dish. However, the *E. coli* mutant strain recovered the ability of growing by compensating the gene to be tested, indicating complementation of the deficient gene.

According to the present invention, the gene cluster involved in the non-mevalonate pathway of *Hevea brasiliensis* was obtained, and the nucleotide sequences of these genes were determined. The gene cluster according to present invention involved in IPP biosynthesis of the non-mevalonate pathway is involved in the biosynthesis of vitamin E and carotenoids. Therefore, practical use plants with high contents of vitamin E and carotenoids can be produced, by transforming plants by the gene cluster obtained in the present invention. More specifically, the *Hevea brasiliensis* obtained by introducing the gene cluster of the present invention can be expected to produce high-quality rubber with improved permanence.

The invention claimed is:

1. An expression vector comprising a nucleotide sequence which encodes the protein of SEQ ID NO: 6.
2. An expression vector comprising the nucleotide sequence of nucleotides 180 to 1115 of SEQ ID NO:5.
3. An expression vector comprising the nucleotide sequence of nucleotides 214 to 1146 of SEQ ID NO:5.
4. An expression vector comprising the nucleotide sequence of nucleotides 1 to 1301 of SEQ ID NO:5.
5. An expression vector comprising the nucleotide sequence of nucleotides 1 to 1335 of SEQ ID NO:5.
6. A transgenic plant, wherein properties of the rubber produced from said plant is improved by introducing the gene according to any one of claims 1 to 5 into said plant.
7. A method to improve the property of the rubber produced from said plant, the method comprising introduction of the gene according to any one of claims 1 to 5 into said plant.

* * * * *